(12) United States Patent
Giralt Lledó et al.

(10) Patent No.: US 9,475,840 B2
(45) Date of Patent: Oct. 25, 2016

(54) PROTEASE-RESISTANT COMPOUNDS USEFUL AS SHUTTLES THROUGH THE BLOOD-BRAIN BARRIER AND SHUTTLE-CARGO CONSTRUCTS

(71) Applicants: UNIVERSITAT DE BARCELONA, Barcelona (ES); FUNDACIÓ INSTITUT DE RECERCA BIOMÈDICA (IRB BARCELONA), Barcelona (ES)

(72) Inventors: Ernest Giralt Lledó, Sant Just Desvern (ES); Meritxell Teixidó Turà, Sant Joan Despi (ES); Roger Prades Cosano, L'Hospitalet de Llobregat (ES)

(73) Assignees: UNIVERSITAT DE BARCELONA, Barcelona (ES); FUNDACIÓ INSTITUT DE RECERCA BIOMÈDICA (IRB BARCELONA), Barcelona (ES)

( * ) Notice: Subject to any disclaimer, the term of this patent is extended or adjusted under 35 U.S.C. 154(b) by 80 days.

(21) Appl. No.: 14/379,484

(22) PCT Filed: Feb. 27, 2013

(86) PCT No.: PCT/EP2013/053892
§ 371 (c)(1),
(2) Date: Aug. 18, 2014

(87) PCT Pub. No.: WO2013/127829
PCT Pub. Date: Sep. 6, 2013

(65) Prior Publication Data
US 2015/0044140 A1   Feb. 12, 2015

(30) Foreign Application Priority Data

Feb. 27, 2012 (ES) .................................. 201230294

(51) Int. Cl.
| | | |
|---|---|---|
| *C07K 7/08* | (2006.01) | |
| *A61K 49/00* | (2006.01) | |
| *A61K 49/18* | (2006.01) | |
| *A61K 31/198* | (2006.01) | |
| *A61K 39/395* | (2006.01) | |
| *A61K 47/48* | (2006.01) | |

(52) U.S. Cl.
CPC ............. *C07K 7/08* (2013.01); *A61K 31/198* (2013.01); *A61K 39/39533* (2013.01); *A61K 47/48238* (2013.01); *A61K 47/48246* (2013.01); *A61K 49/0056* (2013.01); *A61K 49/0093* (2013.01); *A61K 49/1866* (2013.01)

(58) Field of Classification Search
None
See application file for complete search history.

(56) References Cited

U.S. PATENT DOCUMENTS

2007/0231300 A1   10/2007  Sasaki et al.

FOREIGN PATENT DOCUMENTS

| WO | WO 02/44329 | 6/2002 |
| WO | WO 2007/098415 | 8/2007 |
| WO | WO 2008/025867 | 3/2008 |
| WO | WO 2009/008725 | 1/2009 |

(Continued)

OTHER PUBLICATIONS

Merriam-Webster, http://www.merriam-webster.com/dictionary/construction; visited Jan. 9, 2016.*

(Continued)

*Primary Examiner* — Lianko Garyu
(74) *Attorney, Agent, or Firm* — Squire Patton Boggs (US) LLP

(57) ABSTRACT

The peptides of formula (I) where: $R_1$ is the group attached to the N-terminal of the first amino acid of the sequence P, optionally via the ligand X, and is selected from H, $CH_3C(=O)—$, and maleimide; X is a biradical selected from $—NH—(CH_2)_r—C(=O)—$, $—C(=O)—(CH_2)_r—C(=O)—$, $—S(CH_2)_r—$, $—S—(CH_2)_r—C(=O)—$, $—O—(CH_2)_r—$, $—S—CH—CH(NH_2)—C(=O)—$, $—O—(CH_2)_r—C(=O)—$, $—(CH_2)_r—C(=O)—$, $—NH—O—CH_2—C(=O)—NH—(CH_2)_r—CH(NH_2)—C(=O)—$, $—(CH_2)_r—C(=O)—NH—(CH_2)_r—CH(NH_2)—C(=O)—$, and $—NH—(CH_2)_r—CH(NHC(=O)CH_2NH_2)—C(=O)—$; r is 1-5; P is a biradical of an amino acid sequence comprising the sequence D-Pro-D-Trp-D-Val-D-Pro-D-Ser-D-Trp-D-Met-D-Pro-D-Pro-D-Arg-D-His-D-Thr (SEQ ID NO: 1); Y is the group attached to the C-terminal of the last amino acid of the sequence P, and is selected from $—NH_2$, $—OH$, $—OR_2$ and $—NHR_2$; $R_2$ is a radical selected from $(C_1-C_6)$-alkyl and $(CH_2)_2—NH—C(=O)—CH_2—O—NH_2$; k is 0-2; m is 0-1; with the proviso that when the biradical X is $—C(=O)(CH_2)_r—C(=O)—$, then $R_1$ is H; when the N of the amino acid of the sequence P to which is attached the biradical X is a biradical $—NH—$, then m is 1, and when is a biradical $—N—$, then m is 0; and when $R_1$ is maleimide then the biradical X is $—C(=O)—(CH_2)_r—C(=O)—$, $—(CH_2)—C(=O)—$, $—(CH_2)_r—C(=O)—$, and $—(CH_2)_r—C(=O)—NH—(CH_2)_r—CH(NH_2)—C(=O)—$. The peptides are useful as shuttles through the blood brain barrier (BBB). The constructs BBB-shuttle-cargo, being the cargo of a biologically active substance or for use in a diagnostic method, are useful in therapy and diagnosis.

$$R_1—(X)_K—P—Y \qquad (I)$$

18 Claims, No Drawings

(56) References Cited

FOREIGN PATENT DOCUMENTS

WO     WO 2011/009624     1/2011
WO     WO 2012/007625     1/2012

OTHER PUBLICATIONS

Carmen Wangler et al., "In vitro and Initial in vivo Evaluation of Ga-Labeled Transferrin Receptor (TfR) Binding Peptides as Potential Carriers for Enhanced Drug Transport into TfR Expressing Cells" Molecular Imaging and Biology Springer-Verlag, NE vol. 13, No. 2, pp. 332-341, May 15, 2010.
International Search Report for PCT/EP2013/053892 June 27, 2013.
Amblard, et al., "Methods and protocols of modern solid-phase peptide synthesis", Molecular Biotechnology vol. 33, pp. 239-254 (2006).
Gaillard et al. "2B-Trans™ technology: targeted drug delivery across the blood-brain barrier", Methods in Mol. Biol. vol. 437 pp. 161-175 (2008).
Kaiser et al., "Color test for detection of free terminal amino groups in the solid-phase synthesis of peptides", Anal. Biochem. vol. 34, pp. 595-598 (1970).
Lee et al., "Receptor mediated uptake of peptides that bind the human transferrin receptor", in Eur J. Biochem. vol. 268, p. 2004-2012 (2001).
Madder et al., "A novel sensitive colorimetric assay for visual detection of solid-phase bound amines". Eur. J. Org. Chem. pp. 2787-2791(1999).
Temsamani et al,"Improved brain uptake and pharmacological activity profile of morphine-6-glucuronide using a peptide vector-mediated strategy", The J. of Pharmacol. And Exp. Ther. vol. 313, pp. 712-719 (2005).

* cited by examiner

SEQUENCE LISTING

<160> NUMBER OF SEQ ID NOS: 6

<210> SEQ ID NO 1
<211> LENGTH: 12
<212> TYPE: PRT
<213> ORGANISM: Artificial sequence
<220> FEATURE:
<223> OTHER INFORMATION: D amino acids peptide shuttle

```
<400> SEQUENCE: 1

Pro Trp Val Pro Ser Trp Met Pro Pro Arg His Thr
1               5                   10

<210> SEQ ID NO 2
<211> LENGTH: 13
<212> TYPE: PRT
<213> ORGANISM: Artificial sequence
<220> FEATURE:
<223> OTHER INFORMATION: D amino acids peptide shuttle

<400> SEQUENCE: 2

Gly Pro Trp Val Pro Ser Trp Met Pro Pro Arg His Thr
1               5                   10

<210> SEQ ID NO 3
<211> LENGTH: 7
<212> TYPE: PRT
<213> ORGANISM: Artificial sequence
<220> FEATURE:
<223> OTHER INFORMATION: cargo D- amino acids
<220> FEATURE:
<221> NAME/KEY: MOD_RES
<222> LOCATION: (2)..(2)
<223> OTHER INFORMATION: Xaa at position 2 is N-methylphenylalanine
<220> FEATURE:
<221> NAME/KEY: MOD_RES
<222> LOCATION: (3)..(3)
<223> OTHER INFORMATION: Xaa at position 3 is N-naphtylalanine

<400> SEQUENCE: 3

Ala Xaa Xaa Val Leu Lys Lys
1               5

<210> SEQ ID NO 4
<211> LENGTH: 19
<212> TYPE: PRT
<213> ORGANISM: Artificial sequence
<220> FEATURE:
<223> OTHER INFORMATION: Cargo coupled to shuttle peptide
<220> FEATURE:
<221> NAME/KEY: MOD_RES
<222> LOCATION: (2)..(2)
<223> OTHER INFORMATION: Xaa at position 2 is N-methylphenylalanine
<220> FEATURE:
<221> NAME/KEY: MOD_RES
<222> LOCATION: (3)..(3)
<223> OTHER INFORMATION: Xaa at position 3 is N-napthylalanine

<400> SEQUENCE: 4

Ala Xaa Xaa Val Leu Lys Lys Pro Trp Val Pro Ser Trp Met Pro Pro
1               5                   10                  15

Arg His Thr

<210> SEQ ID NO 5
<211> LENGTH: 12
<212> TYPE: PRT
<213> ORGANISM: Artificial sequence
<220> FEATURE:
<223> OTHER INFORMATION: L-amino acids peptide

<400> SEQUENCE: 5

Thr His Arg Pro Pro Met Trp Ser Pro Val Trp Pro
1               5                   10
```

```
<210> SEQ ID NO 6
<211> LENGTH: 12
<212> TYPE: PRT
<213> ORGANISM: Artificial sequence
<220> FEATURE:
<223> OTHER INFORMATION: D-amino acids peptide

<400> SEQUENCE: 6

Thr His Arg Pro Pro Met Trp Ser Pro Val Trp Pro
1               5                   10
```

PROTEASE-RESISTANT COMPOUNDS USEFUL AS SHUTTLES THROUGH THE BLOOD-BRAIN BARRIER AND SHUTTLE-CARGO CONSTRUCTS

RELATED APPLICATIONS

This application is a national stage entry of International Patent Application No. PCT/EP2013/053892 filed on Feb. 27, 2013, which claims the benefit of ES Patent Application No. 201230294 filed on Feb. 27, 2012, which is incorporated by reference herein in its entirety.

The present invention relates to the fields of medicine, research and diagnostics, and more specifically to novel compounds that act as shuttles through the blood-brain barrier (BBB) for the delivery of substances that cannot cross the BBB by themselves. It also refers to shuttle-cargo constructs and their use in therapy or diagnostics.

BACKGROUND ART

Several severe health disorders require treatment of the brain. This includes neurodegenerative diseases such as Parkinson and Alzheimer diseases, but also central nervous system diseases such as schizophrenia, epilepsy or bipolar disorder, brain cancer, human immunodeficiency virus (HIV) and even certain aspects of obesity. The pharmaceutical targets of these diseases are located inside the brain.

The BBB is a natural filter within the body that regulates the passage substances through from the blood to the brain, allowing only certain substances to cross from the blood to the brain. It is a natural defense mechanism designed to keep harmful substances out of the brain. It controls the composition of the brain extracellular fluid independent of fluctuations within the blood. It is also impermeable for many environmental compounds and drugs.

The anatomical basis of the BBB is primarily the tight junction at endothelial cells of cerebral microvessels, which form a continuous membrane with no fenestrations. Specific transporters mediate the access of certain molecules important for the brain, such as glucose, isolated amino acids and ions. Other compounds can cross the BBB by a passive diffusion process through the endothelial cells that form the brain microvessels. However, this process requires a certain degree of lipophylicity of these compounds. This type of transport has the disadvantage of being very selective and to be regulated to some extent by efflux pumps, located in the membrane of endothelial cells that form the BBB, which prevent the accumulation of substances potentially toxic or unnecessary in the nervous system.

In the therapeutic areas mentioned above, many promising compounds are known for their treatment, however, owing to their BBB transport problems, they are not further developed. Research in these fields has taken several approaches.

Some methods of administration of drugs to the brain either for therapy or diagnosis are invasive techniques, such as intracranial administration, administration altering BBB integrity or osmotic disruption. However, these methods imply risk of infection and toxicity, and in addition, require qualified personnel.

Another approach is drug modification. These modifications include for instance reduction of drug size or increase of drug lipophylicity, but it is not always possible to introduce such modifications. In the case of introducing an irreversible modification it is necessary that it doesn't alter the drug activity once it gets to the target site. In the case of a bioreversible modification, it is necessary to find an enzymatic or chemical process that will recover the active drug once the prodrug is inside the central nervous system.

Another approach is the administration of the drug by conjugation to a biological carrier. This strategy is based on the conjugation of the drug to a substrate of a specific protein receptor or to an antibody that recognizes selectively a given receptor, e.g. the transferrin receptor or the receptor of LDL. This drug-carrier conjugate can be recognized by a particular receptor and undergoes a receptor-mediated endocytosis process into the nervous system, in such a way that compounds with a potential therapeutic use which cannot cross the BBB by themselves became able to cross this barrier when are conjugated with the carrier.

Finally, another approach comprises a peptide vector-mediated strategy in which non-transportable drugs are linked to peptides that have the capacity to cross the BBB (cf. J. Temsamani et al., "Improved Brain Uptake and Pharmacological Activity Profile of Morpholine-6-Glucuronide Using a Peptide Vector-Mediated Strategy" in *J. Pharmacol. Exp. Ther.* 2005 vol. 313, pp. 712-719). This approach it has been use to improve the brain uptake of several drugs, such as doxorubicin, penicillin, enkephalin analog dalargin, paclitaxel and morphine-6-glucuronide. In some cases, this conjugation even increased drug solubility and bypassed the P-glycoprotein expressed in the BBB.

WO2008025867 describes several compounds based on the structure of the diketopiperazine that act as vehicles for delivery active pharmaceutical ingredients through the BBB due to they have the capacity to carry drugs that lack capacity to pass the BBB, into the brain by passive diffusion. The permeability of the construct cargo-shuttle through the BBB was studied by means of the PAMPA assay, an in vitro model of the BBB.

Likewise, WO2012007625 describes the use of phenyl proline (PhPro) rich peptides as shuttles of compounds that are unable to cross the BBB. The described peptides can facilitate the transport of these compounds into the central nervous system. This patent application, as WO2008025867, is based in the use of shuttles that are able to cross the BBB by a passive diffusion mechanism. This fact limits their use as shuttles to the transport of small molecules.

Several peptides have been described whose mechanism of transport across the BBB is through an active transport process of receptor-mediated transcytosis.

WO200244329 describes a peptide, THRPPMWSPVWP (SEQ ID NO:5) (L-amino acids), which have the capacity to bind to the human transferrin receptor (hTfR) and internalized into cells expressing hTfR. This peptide can be link to other molecules, such as other peptides or proteins, in order to facilitate the transport of these molecules into cells expressing hTfR. The peptide and its ability to bind hTfR also described in Lee et al., in *Eur J. Biochem.* 2001, vol. 268, p. 2004-2012.

WO2007098415 describes that the peptide THRPPMWSPVWP (SEQ ID NO:5) (L-amino acids) can be used in vivo in order to direct macromolecules into cells expressing hTfR. In particular it is indicated that enhances release of peptide derivatives that inhibit the interaction of proliferating cell nuclear antigen (PCNA) in a specific manner and thus reduce cellular proliferation of malignant cells that express an isoform cancer specific caPCNA. Unfortunately, the peptide THRPPMWSPVWP (SEQ ID NO:5) (L-amino acids) shows a low half-life time in human serum, thus, limiting their applications.

Finally, WO2009008725 describes peptides or peptidomimetics comprising the sequence THRPPMWSPVWP (SEQ ID NO:5) (L-amino acids), as well as the conjugates that comprise these peptides and biological molecules or diagnostic, and their use to direct diagnostic biological molecules across the blood-brain barrier, brain cells, neuronal cells or tumor cells of neuroectodermal origin or neurons for the treatment of related disorders. The peptidomimetics described refers to variants of the above peptide comprising an amino acid substitution in the sequence for another amino acid or derivative of this one. Also describes that the peptide may consist entirely of L-amino acids or may contain one or more modifications in the backbone or side chains. All examples of the application refer to L-amino acids.

On basis of the existing results, it would be desirable to have a compound with the capacity to cross the BBB able to transport cargos across it in an efficient manner. Likewise, it would be interesting that these compounds had a high stability in physiological conditions in order to avoid side effects and improve its efficiency.

SUMMARY OF THE INVENTION

Inventors have found that the peptide PWVPSWMPPRHT (SEQ ID NO: 1) (D-amino acids) and the peptide GPWVPSWMPPRHT (SEQ ID NO: 2) (D-amino acids except the glycine that does not have chirality), have the capacity to cross the BBB and are able to facilitate the transport into the brain of drugs or other substances useful for diagnosis, referred to as "cargos", which cannot cross the BBB by themselves. The peptides are biocompatible, have lack of toxicity and antigenicity as they are made of amino acids. Henceforth, these peptides will be referred as shuttle compounds.

The mechanism of transport of the invention peptides across the BBB is by means of a receptor-mediated transcytosis through the transferrin receptor. This mechanism depends on the configuration L or D of the amino acids. In contrast to it was expected, the peptide compounds of this invention are also recognized by the hTfR receptor and have a surprising improved capacity to operate as shuttles respect to the peptide THRPPMWSPVWP (SEQ ID NO:5) (L-amino acids). The peptides have the capacity to internalize in brain endothelial cells and astrocytes. In addition to this have an improved apparent permeability across the BBB in comparison to the THRPPMWSPVWP (SEQ ID NO:5) sequence (L-amino acids).

The peptide compounds of this invention also show a good solubility in water and a high stability in front of the proteases found in the blood. To be more precise, the peptides have large half-life times in human plasma, given that are resistant to the proteases found in this one. The peptides also show a high stability in front the peptidases associated with the brain microvessels. This property of the compounds of the invention allows improving the administration dose since the amount of solution containing the construct to be administered will be lower.

Thus, a first aspect of the present invention refers to the provision of shuttle compounds of formula (I), or their pharmaceutically acceptable salts,

$$R_1-(X)_K-P-Y, \quad (I)$$

wherein: $R_1$ is the group attached to the N-terminal of the first amino acid of the sequence P, optionally via the ligand X, and is selected from the group consisting of H, $CH_3C(=O)-$, and maleimide; X is a biradical selected from the group consisting of $-NH-(CH_2)_r-C(=O)-$, $-C(=O)-(CH_2)_r-C(=O)-$, $-S(CH_2)_r-$, $-S-(CH_2)_r-C(=O)-$, $-O-(CH_2)_r-$, $-S-CH_2-CH(NH_2)-C(=O)-$, $-O-(CH_2)_r-C(=O)-$, $-(CH_2)_r-C(=O)-$, $-NH-O-CH_2-C(=O)-NH-(CH_2)_r-CH(NH_2)-C(=O)-$, $-(CH_2)_r-C(=O)-NH-(CH_2)_r-CH(NH_2)-C(=O)-$, and $-NH-(CH_2)_r-CH(NHC(=O)CH_2NH_2)-C(=O)-$; wherein the biradical X is attached to $R_1$ and to the N of the sequence P as follows: $R_1-NH-(CH_2)_r-C(=O)-N(H)_m-$, $R_1-C(=O)-(CH_2)_r-C(=O)-N(H)_m-$, $R_1-S-(CH_2)_r-N(H)_m-$, $R_1-S-(CH_2)_r-C(=O)-N(H)_r-$, $R_1-O-(CH_2)_r-N(H)_r-$, $R_1-S-CH_2-CH(NH_2)-C(=O)-N(H)_m-$, $-R_1-O-(CH_2)_r-C(=O)-N(H)_m-$, $R_1-(CH_2)_r-C(=O)-N(H)_m$, $R_1-NH-O-CH_2-C(=O)-NH-(CH_2)_r-CH(NH_2)-C(=O)-N(H)_m$, $R_1-(CH_2)_r-C(=O)-NH-(CH_2)_r-CH(NH_2)-C(=O)-N(H)_m-$, —, and $R_1-NH-(CH_2)_r-CH(NHC(=O)CH_2NH_2)-C(=O)-N(H)_m$; r is an integer from 1 to 5; P is a biradical of an amino acid sequence comprising the sequence D-Pro-D-Trp-D-Val-D-Pro-D-Ser-D-Trp-D-Met-D-Pro-D-Pro-D-Arg-D-His-D-Thr (SEQ ID NO: 1); Y is the group attached to the C-terminal of the last amino acid of the sequence P, and is selected from the group consisting of $-NH_2$, $-OH$, $-OR_2$ and $-NHR_2$; $R_2$ is a radical selected from the group consisting of $(C_1-C_6)$-alkyl and $(CH_2)_2-NH-C(=O)-CH_2-O-NH_2$; k is an integer from 0 to 2; m is an integer from 0 to 1; with the proviso that when the biradical X is $-C(=O)(CH_2)_1C(=O)-$, then $R_1$ is H; with the proviso that when the N of the amino acid of the sequence P to which is attached the biradical X is a biradical $-NH-$, then m is 1, and when is a biradical $-N-$, then m is 0; and with the proviso that when $R_1$ is maleimide then the biradical X is $-C(=O)-(CH_2)_r-C(=O)-$, $-CH(NH_2)-C(=O)-$, $-(CH_2)_r-C(=O)-$, and $-(CH_2)_r-C(=O)-NH-(CH_2)_r-CH(NH_2)-C(=O)-$.

In a preferred embodiment, the compounds of formula (I) are those where: $R_1$ is the group attached to the N-terminal of the first amino acid of the sequence P, optionally via the ligand X, and is selected from the group consisting of H, and $CH_3C(=O)-$; X is a biradical selected from the group consisting of $-NH-(CH_2)_r-C(=O)-$, $-C(=O)-(CH_2)_r-C(=O)-$, $-S-(CH_2)_r-$, $-S-(CH_2)_r-C(=O)-$, $-O-(CH_2)_r-$, $-S-CH_2-CH(NH_2)-C(=O)-$ and $-O-(CH_2)_r-C(=O)-$; wherein the biradical X is attached to $R_1$ and to the N of the sequence P as follows: $R_1-NH-(CH_2)_r-C(=O)-N(H)_m-$, $R_1-C(=O)-(CH_2)_r-C(=O)-N(H)_m-$, $R_1-S-(CH_2)_r-N(H)_m-$, $R_1-S-(CH_2)_r-C(=O)-N(H)_r-$, $R_1-O-(CH_2)_r-N(H)_m-$, $R_1-S-CH_2-CH(NH_2)-C(=O)-N(H)_m$, and $R_1-O-(CH_2)_r-C(=O)-N(H)_m-$; r is an integer from 1 to 3; P is a biradical of an amino acid sequence comprising the sequence D-Pro-D-Trp-D-Val-D-Pro-D-Ser-D-Trp-D-Met-D-Pro-D-Pro-D-Arg-D-His-D-Thr (SEQ ID NO: 1); Y is the group attached to the C-terminal of the last amino acid of the sequence P, and is selected from the group consisting of $-NH_2$, $-OH$, $-OR_2$ and $-NHR_2$; $R_2$ is a radical $(C_1-C_6)$-alkyl; k is an integer from 0 to 2; m is an integer from 0 to 1; with the proviso that when the biradical X is $-C(=O)(CH_2)_1C(=O)-$, then $R_1$ is H and with the proviso that when the N of the amino acid of the sequence P to which is attached the biradical X is a biradical $-NH-$, then m is 1, and when is a biradical $-N-$, then m is 0.

The compounds of formula (I) or their salts may exist in solvated as well as unsolvated forms, including hydrated forms. Thus, in their structure may contain stoichiometric amounts of solvent in the case of solvates, or water in the case of hydrates. It should be understood that this invention encompasses all the solvated forms, as well as unsolvated. Obtaining solvates and hydrates depends on the solvent used and the crystallization conditions that can be determined by the person skilled in the art.

In a preferred embodiment, the peptide compounds of formula (I) are those wherein P is a biradical consisting of SEQ ID NO: 1 and m is 0.

In another preferred embodiment, the peptide compound of formula (I) are those wherein P is a biradical based in the sequence Gly-D-Pro-D-Trp-D-Val-D-Pro-D-Ser-D-Trp-D-Met-D-Pro-D-Pro-D-Arg-D-His-D-Thr (SEQ ID NO: 2) and m is 1.

In a more preferred embodiment, compounds of formula (I) are those wherein Y is —NH$_2$, —OH or —NHR$_2$. In another even more preferred embodiment, compounds of formula (I) are those wherein Y is —NH$_2$. In another preferred embodiment, compounds of formula (I) are those wherein Y is —NHR$_2$, wherein R$_2$ is (CH$_2$)$_2$—NH—C(=O)—CH$_2$—O—NH$_2$.

Preferably, the compounds of formula (I) are those where k is 0 or 1.

The peptide compounds of formula (I) more preferred are those selected from the group consisting of:

H-D-Pro-D-Trp-D-Val-D-Pro-D-Ser-D-Trp-D-Met-D-Pro-D-Pro-D-Arg-D-His-D-Thr-NH$_2$ (SEQ ID NO: 1); and H-Gly-D-Pro-D-Trp-D-Val-D-Pro-D-Ser-D-Trp-D-Met-D-Pro-D-Pro-D-Arg-D-His-D-Thr-NH$_2$ (SEQ ID NO: 2).

In the present document these peptides are referred as indicated above or as PWVPSWMPPRHT (SEQ ID NO: 1) (D-amino acids) or GPWVPSWMPPRHT (SEQ ID NO: 2) (D-amino acids), respectively.

As explained in Example 21, the compounds of formula (I) have the capacity to transport substances into the brain, referred as cargos, which cannot cross the BBB by themselves. Thus, another aspect of the invention relates to the use of these compounds of formula (I) as BBB-shuttles. The use of these compounds makes it possible for instance that the research of novel drugs is not only limited to the compounds that can cross the BBB by themselves. As illustrated by the comparative examples, the compounds of formula (I) are better BBB shuttles than the closest prior art compounds.

The compounds of formula (I) have appropriate functional groups suitable for covalent attachment of cargos maintaining the original activity of the cargo, until it reaches the site of action. Thus, another aspect of the present invention is the provision of constructs of formula (II) or their pharmaceutically acceptable salts, which are referred as BBB shuttle-cargo constructs,

(Z)$_q$—(X)$_K$—P—Y, (II)

wherein: X, P, Y, k are as defined above; q is an integer from 1 to 2, and Z is a radical of a biologically active substance or a substance for use in a diagnostic method, said substance being substantially unable to cross the BBB by itself; wherein when q is 1, then Z is attached to the N-terminal of the first amino acid of the sequence P, optionally via the ligand X, and when q is 2, then one Z is attached to the N-terminal of the first amino acid of the sequence P, optionally via the ligand X, and the other Z is attached to a nitrogen of the biradical X.

In a preferred embodiment, in the constructs of formula (II) or their pharmaceutically acceptable salts q is 1, and have the following formula

Z—(X)$_K$—P—Y, (II')

where: X, P, Y, k are as defined above for the compounds of formula (I) and Z is a radical of a biologically active substance or a substance for use in a method of diagnosis, which is substantially unable to cross the BBB by itself.

The term "substantially unable to cross the BBB" means that it is not capable of crossing the BBB, or if it does is in an amount that is therapeutically non-effective.

Preferred values of X, P, Y, and k, for the compound of formula (I) are also preferred values for the construct of formula (II).

Thus, in a preferred embodiment, the constructs of formula (II) are those where P is selected from the group consisting of a biradical of the sequence SEQ ID NO: 2 and a biradical of the sequence SEQ ID NO: 1.

In another preferred embodiment, the constructs of formula (II) are those where k is an integer from 0 to 1.

In another preferred embodiment the construct of formula (II) are those wherein Y is —NH$_2$, —OH or —NHR$_2$. In a more preferred embodiment, Y is NH$_2$. In another preferred embodiment Y is —NHR$_2$, wherein R$_2$ is (CH$_2$)$_2$—NH—C(=O)—CH$_2$—O—NH$_2$.

The substances from which radical Z is derived include a wide range of substances having pharmacological or diagnostic utility. These substances can be active pharmaceutical ingredients, in particular, antiretroviral agents, anticancer agents, anti-psychotic agents, antineurodegenerative agents or antiepileptic drugs. In a preferred embodiment, Z is a radical derived from an active pharmaceutical ingredient capable of forming an amide bond, an ester bond, a disulfide bond. Alternatively, Z is a radical derived from an active pharmaceutical ingredient capable of forming a thioeter bond, an oxime bond, an amine bond, or a hydrazone bond with X, the mentioned active ingredient being unable to cross the BBB by themselves.

Example of active pharmaceutical ingredient is dopamine. Dopamine is a key neurotransmitter in the central nervous system; in particular, striatal dopamine depletion is associated with clinical conditions of Parkinsonism. Dopamine shown interesting properties as a drug but cannot cross the BBB. In particular, as illustrated in the examples, the constructs of formula (II) allow dopamine to be useful as a drug without having the undesired side effects of the actual therapy, and being a simpler and none invasive technique compared with the existing ones.

Other possible cargos are, for example, peptides, proteins, polymers and antibodies, which have applications as therapeutic or diagnosis agents but that are unable to cross the BBB properly. In a particular embodiment, the peptide is H-D-Ala-D-NMePhe-D-Nal(2)-D-Val-D-Leu-D-Lys-D-Lys (SEQ ID NO: 3). This peptide is useful for the treatment of Alzheimer's disease. In a particular embodiment, antibodies are used as cargos. In a preferred embodiment the antibody is bevacizumab (Avastin). This antibody is useful for the treatment of cancer.

Substances derived from Z also include other substances that would be interesting to transport to the brain but they do not do it properly by themselves, for example contrast agents for magnetic resonance imaging (MRI). Among clinical devices used for clinical cancer diagnosis, MRI outstands as non-invasive and non-destructive powerful imaging modality that provides internal images of living organisms with no limits in the depth of analysis and with a resolution of 10 to 100 microns. It is a valuable technique widely used in cancer diagnosis and research. For early detection of cancer (as well as other diseases) is interesting the use of contrast agents, which can be selectively directed to specific markers located in certain tissues, creating a small accumulation of contrast agent in this tissue. This small accumulation of contrast agent is enough to detect unequivocally the existence, for example, of a tumor in very early states. Contrast agents can also be used as diagnostic methods for other diseases of the central nervous system such as Alzheimer's disease, or as a tool for pre-operative MRI scan that will guide the surgeon. In all these cases the contrast agent used needs to cross the BBB. Examples of typical contrast agents includes include chelates of paramagnetic elements such as gadolinium or manganese (effect on T1), or the use of superparamagnetic nanoparticles of iron oxide (SPION nanoparticles) (T2 effect). Iron oxide nanoparticles are iron oxide particles with diameters between about 1 and 100 nanometers. The two main forms are magnetite ($Fe_3O_4$) and its oxidized form maghemite ($\gamma$-$Fe_2O_3$). They have attracted extensive interest due to their superparamagnetic properties and their potential applications in many fields (although Cu, Co and Ni are also highly magnetic materials, they are toxic and easily oxidized). Superparamagnetism is a form of magnetism, which appears in small ferromagnetic or ferrimagnetic micro or nanoparticles, every particle consisting of one magnetic domain. A magnetic domain is a region within a magnetic material which has uniform magnetization. This means that the individual magnetic moments of the atoms are aligned with one another and point in the same direction.

Other no-MRI diagnostic agents include fluorescent dyes or probes such as carboxyfluorescein and its derivatives, rhodamine and its derivatives, or the use of quantum dots (nanoparticles formed by semiconductor materials with high fluorescence quantum yield). The latter, combined with the use of two-photon microscopy, like in the MRI technique, allows in vivo imaging of living organisms in a no-invasive manner, thus allow their use as diagnostic tool.

A quantum dot is a portion of matter (e.g., semiconductor) whose excitons are confined in all three spatial dimensions. Consequently, such materials have electronic properties intermediate between those of bulk semiconductors and those of discrete molecules. Quantum dots are semiconductors whose electronic characteristics are closely related to the size and shape of the individual crystal. Generally, the smaller the size of the crystal, the larger the band gap, the greater the difference in energy between the highest valence band and the lowest conduction band becomes, therefore more energy is needed to excite the dot, and concurrently, more energy is released when the crystal returns to its resting state.

Also in a preferred embodiment the cargo Z includes antibodies useful in diagnostic methods.

The more preferred constructs of formula (II) are those selected from the group consisting of:

L-Dopa-D-Pro-D-Trp-D-Val-D-Pro-D-Ser-D-Trp-D-Met-D-Pro-D-Pro-D-Arg-D-His-D-Thr-$NH_2$ ((IIa); SEQ ID NO: 1 with an L-dopa as cargo or Z group);

H-D-Ala-D-NMePhe-D-Nal(2)-D-Val-D-Leu-D-Lys-D-Lys-D-Pro-D-Trp-D-Val-D-Pro-D-Ser-D-Trp-D-Met-D-Pro-D-Pro-D-Arg-D-His-D-Thr-$NH_2$ ((IIb); SEQ ID NO: 1 with SEQ ID NO:3 as cargo or Z group);

5(6)-Carboxifluorescein-D-Pro-D-Trp-D-Val-D-Pro-D-Ser-D-Trp-D-Met-D-Pro-D-Pro-D-Arg-D-His-D-Thr-$NH_2$ ((IIc); SEQ ID NO: 1 with 5(6)-Carboxifluorescein as cargo or Z group);

Quantum dot-Gly-D-Pro-D-Trp-D-Val-D-Pro-D-Ser-D-Trp-D-Met-D-Pro-D-Pro-D-Arg-D-His-D-Thr-$NH_2$ ((IId); SEQ ID NO: 2 with Quantum dot as cargo or Z group); and SPION-Gly-D-Pro-D-Trp-D-Val-D-Pro-D-Ser-D-Trp-D-Met-D-Pro-D-Pro-D-Arg-D-His-D-Thr-$NH_2$ ((IIe); SEQ ID NO: 2 with SPION as cargo or Z group).

In a particular embodiment constructs of formula (II) are those selected from the group consisting of:

5(6)-Carboxifluorescein-L-Lys(Antibody)-D-Pro-D-Trp-D-Val-D-Pro-D-Ser-D-Trp-D-Met-D-Pro-D-Pro-D-Arg-D-His-D-Thr-$NH_2$ ((IIf); SEQ ID NO: 1 with 5(6)-Carboxifluorescein and an antibody as cargos or Z groups); and Rhodamine b-L-Lys(Antibody)-D-Pro-D-Trp-D-Val-D-Pro-D-Ser-D-Trp-D-Met-D-Pro-D-Pro-D-Arg-D-His-D-Thr-$NH_2$ ((IIg); SEQ ID NO: 1 with Rhodamine b and an antibody as cargos or Z groups).

As mentioned above according to the cargo of the constructions of formula (II), these will be useful in therapy or diagnosis.

Thus, another aspect of the present invention relates to structures of formula (II) as defined above wherein Z is a radical of a biologically active substance being substantially unable to cross the BBB by itself, for use as a medicament. Preferably, the substances with biological activity are pharmaceutical active ingredients, in particular selected from the group of active ingredients mentioned above.

Another aspect of the invention refers to structures of formula (II) where Z is a radical of dopamine for use in the treatment of Parkinson's disease. This can also be formulated as the use of constructs of formula (II) where Z is a radical of dopamine in the preparation of a medicament for the treatment of Parkinson's disease. Therefore, this aspect is related to a method of treatment and/or prophylaxis of a mammal, including a human, suffering from or being susceptible to develop Parkinson's disease, this method comprise the administration of a therapeutically effective amount of a compound of formula (II) with Z being a radical from dopamine, together with pharmaceutically acceptable excipients or carriers.

Another aspect of the invention relates to structures of formula (II) where Z is a peptide radical of the peptide H-D-Ala-D-NMePhe-D-Nal(2)-D-Val-D-Leu-D-Lys-D-Lys-$NH_2$ (SEQ ID NO: 3) for use in treatment of Alzheimer's disease. The use of peptide H-D-Ala-D-NMePhe-D-Nal (2)-D-Val-D-Leu-D-Lys-D-Lys-$NH_2$ (SEQ ID NO: 3) for the treatment of Alzheimer's is described in WO2008050133. This aspect can also be formulated as the use of constructs of formula (II) where Z is a peptide radical of the peptide H-D-Ala-D-NMePhe-D-Nal(2)-D-Val-D-Leu-D-Lys-D-Lys-$NH_2$ (SEQ ID NO: 3) for the preparation of a medicament for the treatment of Alzheimer's disease. Therefore, this aspect also relates to a method for the treatment and/or prophylaxis of a mammal, including a human, suffering from or being susceptible to develop Alzheimer's disease, this method comprise the administration of a therapeutically effective amount of a compound of formula (II) with Z being a peptide radical of the peptide H-D-Ala-D-NMePhe-D-Nal(2)-D-Val-D-Leu-D-Lys-D-Lys-NH2 (SEQ ID NO: 3), together with pharmaceutically acceptable excipients or carriers.

Another aspect of the invention relates to structures of formula (II) where Z is an antibody for use in treatment of cancer. The use of antibodies such as bevacizumab for the treatment of cancer is described in EP973804 but for the case of brain cancer (ex: glioblastoma) the transport of this antibody across the BBB is far from being optimal. This can also be formulated as the use of constructs of formula (II) where Z is an antibody for the preparation of a medicament for the treatment of cancer. Therefore, this aspect also relates to a method for the treatment and/or prophylaxis of a mammal, including a human, suffering from or being susceptible to develop cancer, this method comprise the administration of a therapeutically effective amount of a compound of formula (II) with Z being an antibody, together with diluents, or pharmaceutically acceptable carriers.

Another aspect of the invention relates to structures of formula (II) where Z is a superparamagnetic iron oxide nanoparticle (SPION nanoparticle), a gadolinium or manganese complex, for the use as contrast agent in a diagnostic method for magnetic resonance imaging. This technique is used for the localization and identification of malignant tumours, metastases of these ones or recurrences. It is also use for the diagnosis of Alzheimer's disease. This aspect can be also formulated as the use of a construct of formula (II) where Z is a superparamagnetic iron oxide nanoparticle (SPION nanoparticle), a gadolinium or manganese complex, for the preparation of a contrast agent for a method of magnetic resonance imaging. Preferably, Z is a superparamagnetic iron oxide nanoparticle (SPION nanoparticle).

Is also considered part of the invention a method for the diagnosis of a disease comprising administering to a mammal, including a human in need of such diagnostic a therapeutically effective amount of the construct of formula (II) wherein Z is an superparamagnetic iron oxide nanoparticle, a gadolinium or manganese complex, together with one or more pharmaceutically acceptable excipients or carriers and/or acceptable for diagnosis, to generate image by magnetic resonance imaging and make a diagnosis using this image.

The term "contrast agent" refers to agents that enhance the visibility of certain structures that are otherwise difficult to see during the scanning. These agents are used for injection into the vascular system to a local display.

Another aspect of the invention relates to structures of formula (II) where Z is a radical of a fluorescent compound for use as a fluorescent probe in a method of imaging using two-photon microscopy, obtaining in vivo imaging of living organisms in a non-invasive way, serving as a diagnostic tool. This aspect can also be formulated as use of a construct of formula (II) where Z is a fluorescent compound for the preparation of a fluorescent probe for a method of imaging, for instance, using two-photon microscopy. Examples of suitable fluorescent compounds are 5(6)-carboxyfluorescein, Texas red, rhodamine or quantum dots. Preferably, the fluorescent compound is 5(6)-carboxyfluorescein or quantum dots.

The invention also relates to a method of diagnosis of a disease comprising administering to a mammal, including a human in need of such diagnostic a therapeutically effective amount of the construct of formula (II) where Z is 5(6)-carboxyfluorescein or a quantum dot together with one or more pharmaceutically acceptable excipients or carriers and/or acceptable for diagnosis, for generating an image using dual photon microscopy and diagnose using this image.

The invention also relates to a method of diagnosis of a disease comprising administering to a mammal, including a human in need of such diagnostic a therapeutically effective amount of the construct of formula (II) where Z is an antibody with one or more pharmaceutically acceptable excipients or carriers and/or acceptable for diagnosis for a method of imaging.

The peptide compounds of formula (I) and the constructs shuttle-cargo of formula (II) can be generated wholly or partly by chemical synthesis. The amino acids required for the preparation of compounds of formula (I) are commercially available. The compounds of formula (I) and construct of formula (II) can be prepared easily, for example by synthesis in liquid phase or, preferably, by solid-phase peptide synthesis, for which there are a number of procedures published (cf. M. Amblard, et al., "Methods and protocols of modern solid-phase peptide synthesis. *Molecular Biotechnology* 2006, Vol. 33, p. 239-254). The compounds of formula (I) or the constructs of formula (II) can also be prepared by any combination of liquid phase synthesis and/or solid phase synthesis. For example, by synthesizing the body of the shuttle through solid-phase synthesis and, subsequently removing protecting groups in solution. The binding of the cargo to the shuttle can be performed in solid phase or in solution. Particular shuttle and the binding to specific cargos are disclosed in more detailed in the examples.

Another aspect of the invention relates to pharmaceutical compositions comprising a therapeutically effective amount of the constructs shuttle-cargo of formula (II) as defined above where Z is a radical of a biologically active substance, together with appropriate amounts of pharmaceutically acceptable diluents or carriers.

The term "therapeutically effective amount" as used herein, refers to the amount of a compound that, when administered, is enough to prevent development of, or alleviate to some extent, one or more symptoms of the disease which is addressed. The particular dose of compound administered according to this invention will of course be determined by the particular circumstances surrounding the case, including the compound administered, the via of administration, the particular condition being treated, and similar considerations.

The term "pharmaceutical composition" refers to a mixture of a compound described herein with other chemical components, such as diluents or carriers. The pharmaceutical composition facilitates administration of the compound to an organism.

The terms "pharmaceutically acceptable excipients or carriers" refers to pharmaceutically acceptable material, composition or vehicle. Each component must be pharmaceutically acceptable in the sense of being compatible with the other ingredients of the pharmaceutical composition. It must be also suitable for use in contact with tissues or organs of humans and animals without excessive toxicity, irritation, allergic response, immunogenicity, or other problems or complications commensurate with a benefit/risk ratio.

A composition which comprises a construct according to the present invention may be administered alone or in combination with other treatments, either simultaneously or sequentially, depending on the condition to be treated.

Finally, also form part of the invention the compositions with diagnostic purposes, which have been called contrast agent or fluorescent probes depending on the construct radical Z of formula (II). These compositions comprise an effective amount of the constructs shuttle-cargo of formula (II) as defined above, where Z is a radical of a substance for use in a diagnostic method for MRI or two-photon spectroscopy, this substance being not able to cross the BBB by itself, together with appropriate amounts of pharmaceutically acceptable excipients or carriers and/or acceptable for diagnosis.

The term "diagnostic acceptable" refers to those excipients or carriers suitable for use in diagnostic technology. They should not adversely affect the stability, safety or efficacy of the composition. Generally, the pharmaceutically acceptable excipients or carriers and/or acceptable for diagnosis are physiologically acceptable sterile medium, i.e. isotonic aqueous solutions.

The compositions of the present invention may be administered in parenteral form suitable for injection, infusion or implantation into the body.

In an additional aspect of the invention a kit comprising the contrast agent according to the present invention in a container together with instructions for use in a diagnostic magnetic resonance imaging is provided.

In another aspect of the invention a kit comprising the fluorescent probe according to the present invention in a container together with instructions for use in a diagnostic method by two-photon microscopy is provided.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

Protected amino acids, handles and resins were supplied by: Luxembourg Industries (Tel-Aviv, Israel), Neosystem (Strasbourg, France), Calbiochem-Novabiochem AG (Laufelfingen, Switzerland), Bachem AG (Bubendorf, Switzerland) or Iris Biotech (Marktredwitz, Germany). Other reagents and solvents used are summarized in Table 1.

TABLE 1

Commercials suppliers and reagents used. DCM passed through an Al2O3 column. DMF is stored on molecular sieves 4Å and nitrogen is bubbled in order to eliminate volatile agents.

| Commercial supplier | Reagents and solvents |
| --- | --- |
| Albatros Chem. Inc. | N-hydroxybenzotriazole (HOBt) |
| Aldrich | L-dopa, piperidine, α-ciano-4-hydroxicinnamic acid (ACH), DOWEX MR-3 Mixed Bed, dispers red I, 1,8-diazabicyclo-[5.4.0]-undec-7-ene (DBU), 3-(4,5-dimethyl-2-thiazolyl)-2,5-diphenyl-2H-tetrazolium bromide (MTT), triisopropylsilane (TIS), 1,2-ethanedithiol (EDT), borax, boric acid, 2-(N-morpholino)ethanesulfonic acid hydrate (MES), N-Ethyl-N'-(3-dimethylaminopropyl)carbodiimide, 5(6)-carboxyfluorescein, HEPES, lucifer yellow, NaCl, KCl, CaCl$_2$, MgCl$_2$, NaHCO$_3$, glucose, HBSS, pyridoxal 5'-phosphate, NaIO4, 2-iminothiolane, tris (2-carboxyethyl)phosphine (TCEP), dithiothreitol (DTT), tetrakis(triphenylphosphine)palladium(0), phenylsilane, rhodamine b, trytil chloride, sodium dithioethylcarbamate, 6-maleimidohexanoic acid |
| Applied GL Biochem Shangai | 1-hydroxy-7-azabenzotriazole (HOAt) |
| Cell applications | bovine brain endothelial cells |
| Charles river | wistar rats |
| Corning Costar | transwells (0.33 cm$^2$; pore size 0.4 μm) |
| Jescuder | NaOH |
| KaliChemie | trifluoroacetic acid (TFA) |
| Lonza | culture medium |
| Merck | molecular sieves 4Å, Thin layer chromatography layers (TLC) |
| Micromod | superparamagnetic iron oxide nanoparticles (79-02-201) |
| Millipore | polyvinylidine diFluoride (PVDF) filters 0.45 μm |
| Novabiochem | benzotriazol-1-yl-oxytripyrrolidinophosphonium hexafluorophosphate (PyBOP), N-hydroxisuccinimide (NHS), hydroxylamine Novatag ™ resin |
| Scharlau | dichloromethane (DCM), dimethylformamide (DMF), MeOH, tert-butylmethylether |

TABLE 1-continued

Commercials suppliers and reagents used. DCM passed through an Al2O3 column. DMF is stored on molecular sieves 4Å and nitrogen is bubbled in order to eliminate volatile agents.

| Commercial supplier | Reagents and solvents |
| --- | --- |
| SDS | acetone, MeCN, toluene |
| Thermo Scientific | Slide-A-Lyzer MINI dialysis device floats |
| GE-Healthcare | Nap-5 desalitng columns, Vivaspin 500 MWCO 50 kDa |
| Iris Biotech | All amino acids except otherwise specified. |
| Vall d'Hebron Hospital Pharmacy | Bevacizumab (Avastin ®) |

General Considerations about the Synthesis.

Solid-phase peptide elongation and other solid-phase manipulations were carried out manually in polypropylene syringes fitted with a polyethylene porous disk. Solvents and soluble reagents were removed by suction. Washings between different synthetical steps were carried out with dimethylformamide (DMF) (5×0.5 min) and dichloromethane (DCM) (5×0.5 min) using 10 mL of solvent/g of resin each time.

Identification Tests.

The test used for the identification and control of the synthesis was the following: A) Kaiser colorimetric assay for the detection of solid-phase bound primary amines (E. Kaiser et al., "Color test for detection of free terminal amino groups in the solid-phase synthesis of peptides"; Anal. Biochem. 1970, vol. 34, pp. 595-598); The Kaiser test was performed by washing a small sample of resin (approx. 1 mg) in DMF (4×1 min) and DCM (4×1 min). Three drops of reagent A and six drops of reagent B were added to the resin, the resulting mixture was heated to 110° C. for 3 minutes. The presence of free primary amines beads is indicated by blue resin. B) p-nitro phenyl ester test for secondary amines bound to solid-phase (A. Madder et al., "A novel sensitive colorimetric assay for visual detection of solid-phase bound amines". Eur. J. Org. Chem. 1999, pp. 2787-2791). The p-nitro phenyl ester assay is performed by first washing a small sample of the resin (approx. 1 mg) with DMF (4×1 minutes) and DCM (4×1 minutes). To the resin ten drops of reagent solution (0.002 M p-nitrophenyl ester of disperse red 1 in MeCN) are added and the resulting mixture is heated at 70° C. for 10 minutes. The solution is then decanted and the resin washed with DMF until a transparent supernatant is obtained. The presence of secondary amines is indicated by red colored resin beads.

Protocols Used During the Synthesis of the Constructs of Formula (I) and (II).

the constructs were synthesized at a 200 μmol scale using the following methods and protocols:

Resin Initial Conditioning.

The Fmoc-Rink amide p-MBHA resin was conditioned by washing with DCM (5×30 s) and DMF (5×30 s) followed by a 20% piperidine solution in DMF (2×1 min and 1×10 min) to remove the Fmoc group. Finally, the resin was washed with DMF (5×30 s).

Fmoc Group Removal.

Removal of the 9-fluorenylmethyloxycarbonyl (Fmoc) protecting group was done with 20% (v/v) piperidine in DMF using 2 treatments of 10 minutes each. Two additional treatments with DBU, toluene, piperidine, DMF (5%, 5%, 20%, 70%) (2×5 min) were performed to ensure the removal of the Fmoc group from secondary amines (proline).

Coupling Methods:

Coupling of the First Amino Acid onto the Rink Amide p-MBHA Resin:

N-Protected amino acid (4 eq) and TBTU (4 eq) were added sequentially to the resin in DMF followed by DIEA (8 eq). The mixture was allowed to react with intermittent manual stirring for 1.5 h. The solvent was removed by suction; the resin was washed with DMF (5×30 s) and DCM (5×30 s). The extent of coupling was checked by the Kaiser colorimetric assay.

Coupling of Second Amino Acid and the Following Amino Acids onto the Rink Amide p-MBHA Resin:

The procedure was the same as for the first one, except that the couplings over proline were done using 4 eq of N-protected amino acid, 4 eq of PyBOP, 12 eq of HOAt and 12 eq of DIEA, the reaction was carried out in DMF and the mixture was allowed to react with intermittent manual stirring (3×1.5 h). The removal of the Fmoc group of the prolines, as well as the extend of the coupling was checked by the p-nitro phenyl ester test.

Coupling of the Cargo (Z):

Depending on the nature of the cargo, it will be linked to the BBB-shuttle in solid-phase or in solution.

Coupling of the Cargo in Solid-Phase:

Depending on the nature of the cargo, it will be linked to the BBB-shuttle through different types of chemical bonds.

For Cargos with a COOH Moiety (e.g. L-Dopa, 5(6)-Carboxyfluorescein)

the coupling of the cargo onto the BBB-shuttle was done in solid-phase: the BBB-shuttle provided with a $NH_2$ group was used and was reacted with 4 eq of Cargo-COOH, using 4 eq of PyBOP and 12 eq of HOAt as coupling reagents and 12 eq of DIEA as a base in DMF during 2 h. The mixture was allowed to react with intermittent manual stirring. The solvent was removed by suction, and the resin was washed with DMF (5×30 s) and DCM (5×30 s). The coupling was repeated two more times. The extent of coupling was checked by the p-nitro phenyl test.

Final Cleavage Step:

It was carried out by treating resin with TFA (94%), $H_2O$ (2.5%), EDT (2.5%) and TIS (2.5%) (1×1 h). Tert-butyl ether was added to the obtained product and the mixture was centrifuged (2×8 min). The supernatant was discarded and the pellet was resuspended in a mixture of $H_2O$ and MeCN (1:1). The product was filtered out and lyophilized.

Coupling of the Cargo in Solution:

Cleavage Step from the Resin:

It was carried out by treating resin with TFA (94%), $H_2O$ (2.5%), EDT (2.5%) and TIS (2.5%) (1×1 h). Tert-butyl ether was added to the obtained product and the mixture was centrifuged (2×8 min). The supernatant was discarded and the pellet was resuspended in a mixture of $H_2O$ and MeCN (1:1). The product was filtered out and lyophilized.

The coupling of the cargo with a COOH moiety (e.g. quantum dots, superparamagnetic iron oxide nanoparticles) in solution was performed using the following protocol: 0.01 mmol (2 mg) of N-(3-dimethylaminopropyl)-N'-ethylcarbodiimide and N-hydroxysuccinimide 0.025 mmol (3 mg) were added to 4 mL of a solution of quantum dots or to superparamagnetic iron oxide nanoparticles (2 mg) in MES (50 mM, pH 6.5), the mixture was allowed to react for 30 minutes and 0.08 μmoles of the shuttle were added (0.12 mg). The mixture was allowed to react for 24 h with gentle agitation. Excess peptide and unreacted reagent were removed by dialysis at 4° C. against water for 36 h. The water was changed every 12 hours.

The Coupling of Antibody Cargos:

The linkage of the antibody to the BBB-shuttle could be done by one of the following technologies.

In all cases, the excipients are removed from the antibody formulation (i.e. bevacizumab (Bv) formulation) using size-exclusion chromatography followed by a concentration step using ultracentrifugal filtration to obtain a 20 mg/mL solution. This solution will be referred to as "BvW".

Tech 1—Conjugation at the N-Termini

25 μL of antibody solution (i.e BvW) ($3.3 \cdot 10^{-9}$ mol, $5.0 \cdot 10^{-4}$ g) was diluted with 75 μL of phosphate buffer 25 mM pH 6.5. Pyridoxal 5'-phosphate (PLP) (298 eq, $1.0 \cdot 10^{-7}$ mol, $2.5 \cdot 10^{-5}$ g) was dissolved in 100 μL of phosphate buffer 25 mM and the pH was made up to 6.5 with 1 M HCl. The BvW solution was mixed with the PLP solution and incubated at 20° C. for 48 h. A Nap-5 size exclusion column was used to separate the excess small molecules from the derivatized antibody using phosphate buffer 25 mM pH 6.2. The antibody was concentrated to 100 μL using a Vivaspin 500 with 50 kDa MWCO and washed twice with phosphate buffer 25 mM pH 6.2. The peptide bearing an aminooxy moiety (60 eq, $2.0 \cdot 10^{-7}$ mol) was dissolved in 50 μL of phosphate buffer 25 mM and the pH was made up to 6.2 with 1 M aqueous HCl. The transaminated antibody from the Nap-5 column were mixed with the peptide solution and with 50 μL of a $4 \cdot 10^{-3}$ M solution of aniline (60 eq, $2.0 \cdot 10^{-7}$ mol, $1.9 \cdot 10^{-5}$ g); the mixture was left to react for 48 h. Excess reagents were removed using a Nap-5 size-exclusion column with phosphate buffer 25 mM pH 6.2.

Tech 2—Conjugation at Carbohydrates

25 μL of antibody solution (i.e BvW) ($3.3 \cdot 10^{-9}$ mol, $5.0 \cdot 10^{-4}$ g) was diluted with 75 μL of PBS pH 7.2 and mixed with 10 μL of 0.1 M $NaIO_4$ in water (54 eq, $1.0 \cdot 10^{-6}$ mol, $2.1 \cdot 10^{-4}$ g). The mixture was left to react 2 h at 4° C. preserved from light. A Nap-5 size exclusion column was used to separate the excess small molecules from the derivatized antibody using phosphate buffer 50 mM pH 6.2. The peptide bearing an aminooxy moiety (60 eq, $2.0 \cdot 10^{-7}$ mol) was dissolved in 50 μL of phosphate buffer 25 mM and the pH was made up to 6.2 with 1 M aqueous HCl. The transaminated antibody from the Nap-5 column were mixed with the peptide solution and with 50 μL of a $4 \cdot 10^{-3}$ M solution of aniline (60 eq, $2.0 \cdot 10^{-7}$ mol, $1.9 \cdot 10^{-5}$ g); the mixture was left to react for 48 h. Excess reagents were removed using a Nap-5 size-exclusion column with phosphate buffer 25 mM pH 6.2.

Tech 3—Conjugation Through Lysines

25 μL of antibody solution (i.e BvW) ($3.3 \cdot 10^{-9}$ mol, $5.0 \cdot 10^4$ g) was diluted with 75 μL of PBS pH 7.2 and incubated with 2-iminothiolane (30 eq, $1.0 \cdot 10^{-7}$ mol, $1.4 \cdot 10^{-5}$ g) for 1 h at 20° C. A Nap-5 size exclusion column was used to separate the non-reacted 2-iminothiolane from the thiolated antibody using PBS pH 7.2. The peptide bearing a maleimide moiety (10 eq, $3.3 \cdot 10^{-8}$ mol) was dissolved in 50 μL of PBS and mixed with the oxidized antibody. The mixture is left to react for 2 h at 20° C. Excess peptide is removed using a Nap-5 size-exclusion column using PBS pH 7.2.

Tech 4. Reduction-Alkylation of Interchain Antibody Disulfides 4.1 Limited Disulfide Reduction:

4.1.A. Reduction with DTT:

The antibody solution (i.e. BvW) was diluted (2 mgmL$^{-1}$, 500 μL) and was partially reduced by DTT (3.25 eq) in 0.025 M sodium borate pH 8, 0.025 M NaCl, 1 mM EDTA for 2 h at 37° C. The excess of DTT was purified away from the partially reduced antibody by size exclusion (Nap 5, GE Healthcare following manufacturer instructions). The concentration of antibody-cysteine thiols produced was determined by titrating with DTNB, typically resulting in 3.0 to 4.0 thiols/antibody.

4.1.B. Reduction with TCEP

The antibody solution (i.e. BvW) was diluted (2 mgmL$^{-1}$, 500 μL) and was partially reduced by TCEP (2.5 eq respectively) in 0.025 M sodium borate pH 8, 0.025 M NaCl, 1 mM EDTA for 2 h at 37° C. No purification was needed. The concentration of antibody-cysteine thiols produced was determined by titrating with DTNB, typically resulting in 3.0 to 4.0 thiols/antibody.

4.2 Partial Reoxidation with DTNB after Total Reduction with DTT

The antibody solution (i.e. BvW) was diluted (2 mgmL$^{-1}$, 500 μL) and was totally reduced by DTT (150 eq) in 0.025 M sodium borate pH 8, 0.025 M NaCl, 1 mM EDTA for 2 h at 37° C. The excess of DTT was purified away from the partially reduced antibody by size exclusion (Nap 5, GE Healthcare following manufacturer instructions). The fully reduced antibody was cooled to 0° C. and then treated with 2.0 equivalents of DTNB (0° C., 20 min). Without further purification the antibody was alkylated by following the protocol above (alkylation 1).

4.3 Alkylation

Partially reduced antibody was alkylated with 1.1 molar equiv of 5(6)-carboxifluorescein-L-Lys(maleimido)-D-Pro-D-Trp-D-Val-D-Pro-D-Ser-D-Trp-D-Met-D-Pro-D-Pro-D-Arg-D-His-D-Thr-NH$_2$ or rhodamine b-L-Lys(maleimido)-D-Pro-D-Trp-D-Val-D-Pro-D-Ser-D-Trp-D-Met-D-Pro-D-Pro-D-Arg-D-His-D-Thr-NH$_2$/thiol. The alkylation reaction was performed at 0° C. for 30 min. Cysteine (1 mM final) was used to quench any unreacted, excess of 5(6)-carboxifluorescein-L-Lys(maleimido)-D-Pro-D-Trp-D-Val-D-Pro-D-Ser-D-Trp-D-Met-D-Pro-D-Pro-D-Arg-D-His-D-Thr-NH$_2$ or rhodamine b-L-Lys(maleimido)-D-Pro-D-Trp-D-Val-D-Pro-D-Ser-D-Trp-D-Met-D-Pro-D-Pro-D-Arg-D-His-D-Thr-NH The excess of peptide was removed from the partially reduced antibody by size exclusion (Nap 5, GE Healthcare following manufacturer instructions).

The antibody concentration was quantified using Nanodrop (coef ext molar=222714 M$^{-1}$ cm$^{-1}$).

Characterization of Products:

The identity of the different compounds synthesized with formula I and II (shuttle or combination of shuttle-cargo) was confirmed using mass spectrometry "Matrix Assisted Laser Desorption/Ionization-Mass Spectrometry" (MALDI) (Instrument: MALDI Voyager DE RP time-of-flight (TOF) PE Biosystem) or HPLC-MS (Instrument: Waters model Alliance 2796, quaternary pump, UV/Vis detector model 2487, ESI-MS model Micromass ZQ and software Masslynx version 4.0) using a Symmetry 300 C$_{18}$ (150×3.9 mm×5 μm), 300 Å column using a 1 mL/min flow; solvents: A: H$_2$O with 0.1% formic acid; B: MeCN with 0.07% formic acid. Their purity was checked by reverse phase HPLC using a Symmetry C$_{18}$ column (150×4.6 mm×5 μm, 100 Å, Waters) and a Sunfire C$_{18}$ column (100×4.6 mm×3.5 μm, 100 Å, Waters), flow 1 mL/min; solvents: A: H$_2$O with 0.045% TFA; B: MeCN with 0.036% TFA, Instrument: Waters model Alliance 2695 constituted by a quaternary pump, a diode array detector model 966, controlled by the software Millenium version 3.5.

Constructs including an antibody were characterized by using mass spectrometry "Matrix Assisted Laser Desorption/Ionization-Mass Spectrometry" (MALDI) (Instrument: MALDI Voyager DE RP time-of-flight (TOF) PE Biosystem), SDS page.

SDS-PAGE electrophoresis was carried out using BioRad system (Miniprotean cell) 7.5% Tris gel, 25 mM Tris, 192 mM glycine, 0.1% SDS running buffer). Protein molecular weights were approximated by comparison to a protein marker (Perfect Protein Markers 15-150 kDa from Novagen). Gels were visualised by coomassie staining (staining solution: 10% AcOH, 0.25 g brilliant blue; discoloration solution: 20% MeOH, 3% AcOH glacial, in water). Edman sequencing (first 4 cycles) was used to quantify the amount of peptides conjugated at the N-termini.

Compounds were purified by HPLC using a Symmetry C$_{18}$ column (100×30 mm×5 μm, 100 Å, Waters), flow 15 mL/min, solvents: A: H$_2$O with 0.1% TFA; B: MeCN with 0.1% TFA, Instrument: Waters system with a quaternary pump, Simple Manager 2700 autoinjector, UV/Vis detector model 2487 and a Fraction collector II, controlled by the software Masslynx version 3.5.

EXAMPLES

Example 1

Preparation of H-D-Pro-D-Trp-D-Val-D-Pro-D-Ser-D-Trp-D-Met-D-Pro-D-Pro-D-Arg-D-His-D-Thr-NH$_2$ (SEQ ID NO: 1)

The synthesis was performed on a scale 200 μmol. For the coupling of the first amino acid onto the Fmoc-Rink amide p-MBHA resin the following protocol was used: The protected derivative of the first amino acid (Fmoc-D-Thr(tBu)-OH, 4 eq, 800 μmols, 318 mg) and the coupling agent TBTU (4 eq, 800 μmols, 257 mg) dissolved in DMF (1-3 mL/g resin) were added sequentially to the resin followed by addition of DIEA (8 eq, 1.3 mmol, 267 μl). The mixture was allowed to react with intermittent manual stirring for 1.5 h. The solvent was removed by suction and the resin washed with DMF (5×30 s) and DCM (5×30 s). The extent of coupling was checked by the Kaiser colorimetric assay. The Fmoc group was removed with a 20% (v/v) piperidine in DMF (v/v) using two treatments of 1 min and a treatment of 10 minutes.

The protected amino acid derivative of the second amino acid was coupled to the first amino acid anchored onto the resin using the following protocol: the protected amino acid (Fmoc-D-His(Trt)-OH, 4 eq. 800 μmols, 496 mg), TBTU (4 eq, 800 μmols, 257 mg) dissolved in DMF (1-3 mL/g resin) were added sequentially to the resin, subsequently DIEA was added (8 eq, 1.3 mmol, 267 μL). The mixture was allowed to react with intermittent manual stirring for 1.5 h. The solvent was removed by suction and the resin was washed with DMF (5×30 s) and DCM (5×30 s). The extent of coupling was checked by the Kaiser colorimetric assay. The Fmoc group was removed with a solution of 20% piperidine in DMF (v/v) using two 1 min treatments and 1 treatment of 10 minutes.

The protected amino acid derivative of the third amino acid was coupled to the second amino acid already anchored to the resin using the following protocol: the protected amino acid (Fmoc-D-Arg(Pbf)-OH, 4 eq. 800 μmols, 519 mg), TBTU (4 eq, 800 μmols, 257 mg) dissolved in DMF (1-3 mL/g resin) were added sequentially to the resin, subsequently DIEA was added (8 eq, 1.3 mmol, 267 μL). The mixture was allowed to react with intermittent manual stirring for 1.5 h. The solvent was removed by suction and the resin washed with DMF (5×30 s) and DCM (5×30 s). The extent of coupling was checked by the Kaiser colorimetric assay. The Fmoc group was removed with a 20% solution of piperidine in DMF (v/v) using two 1 min treatments and 1 treatment of 10 minutes.

The protected amino acid derivative of the fourth amino acid was coupled to the third amino acid already anchored to the resin using the following protocol: the protected amino acid (Fmoc-D-Pro-OH, 4 eq. 800 µmols, 270 mg), TBTU (4 eq, 800 µmols, 257 mg) dissolved in DMF (1-3 mL/g resin) were added sequentially to the resin, subsequently DIEA was added (8 eq, 1.3 mmol, 267 µL). The mixture was allowed to react with intermittent manual stirring for 1.5 h. The solvent was removed by suction and the resin washed with DMF (5×30 s) and DCM (5×30 s). The extent of coupling was checked by the Kaiser colorimetric assay. The Fmoc group was removed with a 20% solution of piperidine in DMF (v/v) using two 1 min treatments and 1 treatment of 10 minutes, and treatment with DBU, toluene, piperidine, DMF (5%, 5%, 20%, 70%) (2×5 min) to ensure the removal of the Fmoc group.

The protected amino acid derivative of the fifth amino acid was coupled to the fourth amino acid already anchored onto the resin using the following protocol: the protected amino acid (Fmoc-D-Pro-OH, 4 eq. 800 µmols, 270 mg), PyBOP (4 eq, 800 µmols, 416 mg), HOAt (12 eq, 2.4 mmol, 327 mg) dissolved in DMF (1-3 mL/g resin) were added sequentially to the resin, subsequently DIEA was added (12 eq, 2.4 mmol, 408 µL). The mixture was allowed to react with intermittent manual stirring for 1.5 h. The solvent was removed by suction and the resin washed with DMF (5×30 s) and DCM (5×30 s). The coupling reaction was carried out twice under the same conditions. The extent of coupling was checked by the p-nitro phenyl ester colorimetric assay. The Fmoc group was removed with a 20% solution of piperidine in DMF (v/v) using two 1 min treatments and 1 treatment of 10 minutes, and treatment with DBU, toluene, piperidine, DMF (5%, 5%, 20%, 70%) (2×5 min) to ensure the removal of the Fmoc group.

The protected amino acid derivative of the sixth amino acid was coupled to the fifth amino acid already anchored onto the resin using the following protocol: the protected amino acid (Fmoc-D-Met-OH, 4 eq. 800 µmols, 297 mg), PyBOP (4 eq, 800 µmols, 416 mg), HOAt (12 eq, 2.4 mmol, 327 mg) dissolved in DMF (1-3 mL/g resin) were added sequentially to the resin, subsequently DIEA was added (12 eq, 2.4 mmol, 408 µL). The mixture was allowed to react with intermittent manual stirring for 1.5 h. The solvent was removed by suction and the resin washed with DMF (5×30 s) and DCM (5×30 s). The coupling reaction was carried out twice under the same conditions. The extent of coupling was checked using the p-nitro phenyl ester the colorimetric assay. The Fmoc group was removed with a 20% solution of piperidine in DMF (v/v) using two 1 min treatments and 1 treatment of 10 minutes.

The protected amino acid derivative of the seventh amino acid was coupled to the sixth amino acid already anchored onto the resin using the following protocol: the protected amino acid (Fmoc-D-Trp(Boc)-OH, 4 eq. 800 µmols, 421 mg), TBTU (4 eq, 800 µmols, 257 mg) dissolved in DMF (1-3 mL/g resin) were added sequentially to the resin, subsequently DIEA was added (8 eq, 1.3 mmol, 267 µL). The mixture was allowed to react with intermittent manual stirring for 1.5 h. The solvent was removed by suction and the resin washed with DMF (5×30 s) and DCM (5×30 s). The extent of coupling was checked by the Kaiser colorimetric assay. The Fmoc group was removed with a 20% solution of piperidine in DMF (v/v) using two 1 min treatments and 1 treatment of 10 minutes.

The protected amino acid derivative of the eighth amino acid is coupled to the seventh amino acid already anchored onto the resin using the following protocol: the protected amino acid (Fmoc-D-Ser(tBu)-OH, 4 eq. 800 µmols, 307 mg), TBTU (4 eq, 800 µmols, 257 mg) dissolved in DMF (1-3 mL/g resin) were added sequentially to the resin, subsequently DIEA was added (8 eq, 1.3 mmol, 267 µL). The mixture was allowed to react with intermittent manual stirring for 1.5 h. The solvent was removed by suction and the resin washed with DMF (5×30 s) and DCM (5×30 s). The extent of coupling was checked by the Kaiser colorimetric assay. The Fmoc group was removed with a 20% solution of piperidine in DMF (v/v) using two 1 min treatments and 1 treatment of 10 minutes.

The protected amino derivative of the ninth amino acid was coupled to the eighth amino already anchored onto the resin using the following protocol: the protected amino acid (Fmoc-D-Pro-OH, 4 eq. 800 µmols, 270 mg), TBTU (4 eq, 800 µmols, 257 mg) dissolved in DMF (1-3 mL/g resin) were added sequentially to the resin, subsequently DIEA was added (8 eq, 1.3 mmol, 267 µL). The mixture was allowed to react with intermittent manual stirring for 1.5 h. The solvent was removed by suction and the resin washed with DMF (5×30 s) and DCM (5×30 s). The extent of coupling was checked by the Kaiser colorimetric assay. The Fmoc group was removed with a 20% solution of piperidine in DMF (v/v) using two 1 min treatments and 1 treatment of 10 minutes, and treatment with DBU, toluene, piperidine, DMF (5%, 5%, 20%, 70%) (2×5 min) to ensure the removal of the Fmoc group.

The protected amino acid derivative of the tenth amino acid was coupled to the ninth amino acid already anchored onto the resin using the following protocol: the protected amino acid (Fmoc-D-Val-OH, 4 eq. 800 µmols, 271 mg), PyBOP (4 eq, 800 µmols, 416 mg), HOAt (12 eq, 2.4 mmol, 327 mg), dissolved in DMF (1-3 ml/g resin) were added sequentially to the resin, subsequently DIEA was added (12 eq, 2.4 mmol, 408 µL). The mixture was allowed to react with intermittent manual stirring for 1.5 h. The solvent was removed by suction and the resin washed with DMF (5×30 s) and DCM (5×30 s). The coupling reaction was carried out twice under the same conditions. The extent of coupling was checked by the colorimetric assay of p-nitro phenyl ester. The Fmoc group was removed with a 20% solution of piperidine in DMF (v/v) using two 1 min treatments and 1 treatment of 10 minutes.

The protected amino acid derivative of the eleventh amino acid was coupled to the tenth amino acid already anchored onto the resin using the following protocol: the protected amino acid (Fmoc-D-Trp(Boc)-OH, 4 eq. 800 µmols, 421 mg), TBTU (4 eq, 800 µmols, 257 mg) dissolved in DMF (1-3 mL/g resin) were added sequentially to the resin, subsequently DIEA was added (8 eq, 1.3 mmol, 267 µL). The mixture was allowed to react with intermittent manual stirring for 1.5 h. The solvent was removed by suction and the resin washed with DMF (5×30 s) and DCM (5×30 s). The extent of coupling was checked by the Kaiser colorimetric assay. The Fmoc group was removed with a 20% solution of piperidine in DMF (v/v) using two 1 min treatments and 1 treatment of 10 minutes.

The protected amino acid derivative of the twelfth amino acid was coupled to the eleventh amino acid already anchored onto the resin using the following protocol: the protected amino acid (Fmoc-D-Pro-OH, 4 eq. 800 µmols, 270 mg), TBTU (4 eq, 800 µmols, 257 mg) dissolved in DMF (1-3 mL/g resin) were added sequentially to the resin, subsequently DIEA was added (8 eq, 1.3 mmol, 267 µL).

The mixture was allowed to react with intermittent manual stirring for 1.5 h. The solvent was removed by suction and the resin washed with DMF (5×30 s) and DCM (5×30 s). The extent of coupling was checked by the Kaiser colorimetric assay. The Fmoc group was removed with a 20% solution of piperidine in DMF (v/v) using two 1 min treatments and 1 treatment of 10 minutes, and treatment with DBU, toluene, piperidine, DMF (5%, 5%, 20%, 70%) (2×5 min) to ensure the removal of the Fmoc group.

The cleavage step was performed treating the resin with a mixture of TFA (94%), H$_2$O (2.5%), EDT (2.5%) and TIS (1%) (1×1 h). tert-butyl methyl ether was added to the product obtained and the mixture was centrifuged (2×8 min). The supernatant was removed and the pellet resuspended in a mixture of H$_2$O and MeCN (1:1). The product was filtered and lyophilized.

Product characterization. Reverse phase HPLC: linear gradient from 0 to 100% MeCN in H$_2$O in 8 minutes using a Sunfire C$_{18}$ column (100 mm×4.6 mm, 3.5 mm, 100 Å, Waters), flow of 1 mL/min; Retention time: 5.3 min. Mass spectrometry (MALDI-TOF): [M+H]+: 1489.6; Yield (synthesis and purification): 8.3%.

Example 2

Preparation of H-Gly-D-Pro-D-Trp-D-Val-D-Pro-D-Ser-D-Trp-D-Met-D-Pro-D-Pro-D-Arg-D-His-D-Thr-NH$_2$ (SEQ ID NO: 2)

The procedure of the Example 1 was repeated until the coupling of the twelfth amino acid.

For the coupling of the glycine residue to the BBB-shuttle anchored onto the resin the following protocol was used: Fmoc-Gly-OH (4 eq, 800 μmols, 238 mg) in DMF (1-3 mL/g resin), PyBOP (4 eq, 800 μmols, 416 mg) and HOAt (12 eq, 2.4 mmol, 327 mg) were sequentially added to the resin followed by the addition of 12 eq of DIEA (2.4 mmol, 408 μL). The mixture was allowed to react with intermittent manual stirring for 1.5 h. The solvent was removed by suction, the resin washed with DMF (5×30 s) and DCM (5×30 s). The coupling was repeated twice under the same conditions. The extent of coupling was monitored using the p-nitro phenyl ester test. The Fmoc group was removed with a 20% solution of piperidine in DMF (v/v) using two 1 min treatments a treatment of 10 minutes.

The cleavage step was performed treating the resin with a mixture of TFA (94%), H$_2$O (2.5%), EDT (2.5%) and TIS (1%) (1×1 h). tert-butyl methyl ether was added to the obtained product and the mixture was centrifuged (2×8 min). The supernatant was removed and the pellet resuspended in a mixture of H$_2$O and MeCN (1:1). The product was filtered out and lyophilized.

Product characterization. Reverse phase HPLC: linear gradient from 0 to 100% MeCN in H$_2$O in 8 minutes using a Sunfire C$_{18}$ column (100 mm×4.6 mm, 3.5 mm, 100 Å, Waters), flow of 1 mL/min; Time retention: 4.3 min. Mass spectrometry (MALDI-TOF): [M+H]+: 1849.3; Yield (synthesis and purification): 4.7%.

Example 3

Preparation of H-Gly-D-Pro-D-Trp-D-Val-D-Pro-D-Ser-D-Trp-D-Met-D-Pro-D-Pro-D-Arg-D-His-D-Thr-Aminooxy (SEQ ID NO: 2-Aminooxy)

The procedure of the Example 2 was repeated until the coupling of the thirteenth amino acid using Hydroxylamine Novabiotag™ resin with a substitution of 0.56 mmol/g.

The cleavage step was performed treating the resin with a mixture of TFA (95%), H$_2$O (2.5%), and TIS (2.5%) (1×2 h). tert-butyl methyl ether was added to the obtained product and the mixture was centrifuged (2×8 min). The supernatant was removed and the pellet resuspended in a mixture of H$_2$O and MeCN (1:1). The product was filtered out and lyophilized.

Product characterization. Reverse phase HPLC: linear gradient from 17 to 23% MeCN in H$_2$O in 8 minutes using a Sunfire C$_{18}$ column (100 mm×4.6 mm, 3.5 mm, 100 Å, Waters), flow of 1 mL/min; Time retention: 6.4 min. Mass spectrometry (MALDI-TOF): [M+H]: 1663.9;

Example 4

Preparation of 5(6)-Carboxyfluorescein-L-Lys(Aminooxy)-D-Pro-D-Trp-D-Val-D-Pro-D-Ser-D-Trp-D-Met-D-Pro-D-Pro-D-Arq-D-His-D-Thr-NH$_2$ (SEQ ID NO:1 for the Incorporation of Two Cargos)

The procedure of the Example 1 was repeated until the coupling of the twelfth amino acid.

For the coupling of the Lysine residue to the BBB-shuttle anchored onto the resin the following protocol was used: Fmoc-Lys(Boc$_2$-AoA)-OH (4 eq, 800 μmols, 513 mg) in DMF (1-3 mL/g resin), PyBOP (4 eq, 800 μmols, 416 mg) and HOAt (12 eq, 2.4 mmol, 327 mg) were sequentially added to the resin followed by the addition of 12 eq of DIEA (2.4 mmol, 408 μL). The mixture was allowed to react with intermittent manual stirring for 1.5 h. The solvent was removed by suction, the resin washed with DMF (5×30 s) and DCM (5×30 s). The extent of coupling was monitored using the Kaiser colorimetric assay. The Fmoc group was removed with a 20% solution of piperidine in DMF (v/v) using two 1 min treatments and a treatment of 10 minutes.

For the coupling of the (5)6-carboxyfluorescein to the BBB-shuttle anchored onto the resin the following protocol was used: rhodamine b (4 eq, 800 μmols, 383 mg) in DMF (1-3 mL/g resin), PyBOP (4 eq, 800 μmols, 416 mg) and HOAt (12 eq, 2.4 mmol, 327 mg) were sequentially added to the resin followed by the addition of 12 eq of DIEA (2.4 mmol, 408 μL). The mixture was allowed to react with intermittent manual stirring for 1.5 h. The solvent was removed by suction, the resin washed with DMF (5×30 s) and DCM (5×30 s). The coupling was repeated under the same conditions. The extent of coupling was monitored using the Kaiser colorimetric assay. The Fmoc group was removed with a 20% solution of piperidine in DMF (v/v) using two 1 min treatments a treatment of 10 minutes.

The cleavage step was performed treating the resin with a mixture of TFA (95%), H$_2$O (2.5%), and TIS (2.5%) (1×2 h). Tert-butyl methyl ether was added to the obtained product and the mixture was centrifuged (2×8 min). The supernatant was removed and the pellet resuspended in a mixture of H$_2$O and MeCN (1:1). The product was filtered out and lyophilized.

Product characterization. Reverse phase HPLC: linear gradient from 0 to 100% MeCN in H$_2$O in 8 minutes using a Sunfire C$_{18}$ column (100 mm×4.6 mm, 3.5 mm, 100 Å, Waters), flow of 1 mL/min; Time retention: 5.0 min. Mass spectrometry (MALDI-TOF): [M+H]: 2021.9;

Example 5

Preparation of Maleimide-D-Pro-D-Trp-D-Val-D-Pro-D-Ser-D-Trp-D-Met-D-Pro-D-Pro-D-Arg-D-His-D-Thr-NH$_2$ (SEQ ID NO: 1 with Maleimide as R$_1$)

The procedure of the Example 1 was repeated until the coupling of the twelfth amino acid.

For the coupling of the maleimide to the BBB-shuttle anchored onto the resin the following protocol was used: 6-maleimidohexanoic acid (4 eq, 800 μmols, 169 mg) in DMF (1-3 mL/g resin), PyBOP (4 eq, 800 μmols, 416 mg) and HOAt (12 eq, 2.4 mmol, 327 mg) were sequentially added to the resin followed by the addition of 12 eq of DIEA (2.4 mmol, 408 μL). The mixture was allowed to react with intermittent manual stirring for 1.5 h. The solvent was removed by suction, the resin washed with DMF (5×30 s) and DCM (5×30 s). The extent of coupling was monitored using the Kaiser colorimetric assay.

The cleavage step was performed treating the resin with a mixture of TFA (95%), $H_2O$ (2.5%), and TIS (2.5%) (1×2 h). tert-butyl methyl ether was added to the obtained product and the mixture was centrifuged (2×8 min). The supernatant was removed and the pellet resuspended in a mixture of $H_2O$ and MeCN (1:1). The product was filtered out and lyophilized.

Product characterization. Reverse phase HPLC: linear gradient from 0 to 100% MeCN in $H_2O$ in 8 minutes using a Sunfire $C_{18}$ column (100 mm×4.6 mm, 3.5 mm, 100 Å, Waters), flow of 1 mL/min; Time retention: 5.3 min. Mass spectrometry (MALDI-TOF): [M+H]: 2172.7;

Example 6

Preparation of Rhodamine b-L-Lys(Maleimide)-D-Pro-D-Trp-D-Val-D-Pro-D-Ser-D-Trp-D-Met-D-Pro-D-Pro-D-Arg-D-His-D-Thr-$NH_2$ (SEQ ID NO:1 for the Incorporation of Two Cargos)

The procedure of the Example 1 was repeated until the coupling of the twelfth amino acid.

For the coupling of the Lysine residue to the BBB-shuttle anchored onto the resin the following protocol was used: Fmoc-Lys(alloc)-OH (4 eq, 800 μmols, 362 mg) in DMF (1-3 mL/g resin), PyBOP (4 eq, 800 μmols, 416 mg) and HOAt (12 eq, 2.4 mmol, 327 mg) were sequentially added to the resin followed by the addition of 12 eq of DIEA (2.4 mmol, 408 μL). The mixture was allowed to react with intermittent manual stirring for 1.5 h. The solvent was removed by suction, the resin washed with DMF (5×30 s) and DCM (5×30 s). The extent of coupling was monitored using the Kaiser colorimetric assay. The Fmoc group was removed with a 20% solution of piperidine in DMF (v/v) using two 1 min treatments and a treatment of 10 minutes.

For the coupling of the rhodamine b to the BBB-shuttle anchored onto the resin the following protocol was used: rhodamine b (4 eq, 800 μmols, 383 mg) in DMF (1-3 mL/g resin), PyBOP (4 eq, 800 μmols, 416 mg) and HOAt (12 eq, 2.4 mmol, 327 mg) were sequentially added to the resin followed by the addition of 12 eq of DIEA (2.4 mmol, 408 μL). The mixture was allowed to react with intermittent manual stirring for 1.5 h. The solvent was removed by suction, the resin washed with DMF (5×30 s) and DCM (5×30 s). The coupling was repeated under the same conditions. The extent of coupling was monitored using the Kaiser colorimetric assay. The Fmoc group was removed with a 20% solution of piperidine in DMF (v/v) using two 1 min treatments a treatment of 10 minutes.

For the deprotection of the Alloc protecting group the following protocol was used: tetrakis(triphenylphosphine) palladium(0) (0.1 eq, 20 μmol, 23 mg) in DCM (1-3 mL/g resin) and phenylsilane (10 eq, 2.0 mmol, 247 μL) were sequentially added to the resin. The mixture was allowed to react for 15 min. The solvent was removed by suction. The deprotection was repeated two times under the same conditions. The peptidyl-resin is washed with 3 mL of sodium diethyldithiocarbamate 0.02 M.

For the coupling of the maleimide to the BBB-shuttle anchored onto the resin the following protocol was used: 6-maleimidohexanoic acid (4 eq, 800 μmols, 169 mg) in DMF (1-3 mL/g resin), PyBOP (4 eq, 800 μmols, 416 mg) and HOAt (12 eq, 2.4 mmol, 327 mg) were sequentially added to the resin followed by the addition of 12 eq of DIEA (2.4 mmol, 408 μL). The mixture was allowed to react with intermittent manual stirring for 1.5 h. The solvent was removed by suction, the resin washed with DMF (5×30 s) and DCM (5×30 s). The extent of coupling was monitored using the Kaiser colorimetric assay.

The cleavage step was performed treating the resin with a mixture of TFA (95%), $H_2O$ (2.5%), and TIS (2.5%) (1×2 h). tert-butyl methyl ether was added to the obtained product and the mixture was centrifuged (2×8 min). The supernatant was removed and the pellet resuspended in a mixture of $H_2O$ and MeCN (1:1). The product was filtered out and lyophilized.

Product characterization. Reverse phase HPLC: linear gradient from 0 to 100% MeCN in $H_2O$ in 8 minutes using a Sunfire $C_{18}$ column (100 mm×4.6 mm, 3.5 mm, 100 Å, Waters), flow of 1 mL/min; Time retention: 4.4 min. Mass spectrometry (MALDI-TOF): $[M+H]^+$: 1869.1;

Example 7

Preparation of 5(6)-Carboxyfluorescein-L-Lys(Maleimide)-D-Pro-D-Trp-D-Val-D-Pro-D-Ser-D-Trp-D-Met-D-Pro-D-Pro-D-Arq-D-His-D-Thr-$NH_2$ (SEQ ID NO:1 for the Incorporation of Two Cargos)

The procedure of the Example 1 was repeated until the coupling of the twelfth amino acid.

For the coupling of the Lysine residue to the BBB-shuttle anchored onto the resin the following protocol was used: Fmoc-Lys(alloc)-OH (4 eq, 800 μmols, 362 mg) in DMF (1-3 mL/g resin), PyBOP (4 eq, 800 μmols, 416 mg) and HOAt (12 eq, 2.4 mmol, 327 mg) were sequentially added to the resin followed by the addition of 12 eq of DIEA (2.4 mmol, 408 μL). The mixture was allowed to react with intermittent manual stirring for 1.5 h. The solvent was removed by suction, the resin washed with DMF (5×30 s) and DCM (5×30 s). The extent of coupling was monitored using the Kaiser colorimetric assay. The Fmoc group was removed with a 20% solution of piperidine in DMF (v/v) using two 1 min treatments and a treatment of 10 minutes.

For the coupling of the (5)6-carboxyfluorescein to the BBB-shuttle anchored onto the resin the following protocol was used: rhodamine b (4 eq, 800 μmols, 383 mg) in DMF (1-3 mL/g resin), PyBOP (4 eq, 800 μmols, 416 mg) and HOAt (12 eq, 2.4 mmol, 327 mg) were sequentially added to the resin followed by the addition of 12 eq of DIEA (2.4 mmol, 408 μL). The mixture was allowed to react with intermittent manual stirring for 1.5 h. The solvent was removed by suction, the resin washed with DMF (5×30 s) and DCM (5×30 s). The coupling was repeated under the same conditions. The extent of coupling was monitored using the Kaiser colorimetric assay. The Fmoc group was removed with a 20% solution of piperidine in DMF (v/v) using two 1 min treatments a treatment of 10 minutes.

For the tritylation of the phenol moieties of the carboxylfuorescein the following protocol was used: trityl chloride (12 eq, 2.4 mmol, 223 mg) was added to the resin. The mixture was allowed to react for 16 h. The solvent was removed by suction, the resin washed with DMF (5×30 s) and DCM (5×30 s). The For the deprotection of the Alloc protecting group the following protocol was used: tetrakis(triphenylphosphine) palladium(0) (0.1 eq, 20 µmol, 23 mg) in DCM (1-3 mL/g resin) and phenylsilane (10 eq, 2.0 mmol, 247 µL) were sequentially added to the resin. The mixture was allowed to react for 15 min. The solvent was removed by suction. The deprotection was repeated two times under the same conditions. The peptidyl-resin is washed with 3 mL of sodium diethyldithiocarbamate 0.02 M.

For the coupling of the maleimide to the BBB-shuttle anchored onto the resin the following protocol was used: 6-maleimidohexanoic acid (4 eq, 800 µmols, 169 mg) in DMF (1-3 mL/g resin), PyBOP (4 eq, 800 µmols, 416 mg) and HOAt (12 eq, 2.4 mmol, 327 mg) were sequentially added to the resin followed by the addition of 12 eq of DIEA (2.4 mmol, 408 pt). The mixture was allowed to react with intermittent manual stirring for 1.5 h. The solvent was removed by suction, the resin washed with DMF (5×30 s) and DCM (5×30 s). The extent of coupling was monitored using the Kaiser colorimetric assay.

The cleavage step was performed treating the resin with a mixture of TFA (95%), $H_2O$ (2.5%), and TIS (2.5%) (1×2 h). tert-butyl methyl ether was added to the obtained product and the mixture was centrifuged (2×8 min). The supernatant was removed and the pellet resuspended in a mixture of $H_2O$ and MeCN (1:1). The product was filtered out and lyophilized.

Product characterization. Reverse phase HPLC: linear gradient from 0 to 100% MeCN in $H_2O$ in 8 minutes using a Sunfire $C_{18}$ column (100 mm×4.6 mm, 3.5 mm, 100 Å, Waters), flow of 1 mL/min; Time retention: 5.3 min. Mass spectrometry (MALDI-TOF): [M+H]: 2172.7;

Example 8

Preparation of the compound L-dopa-D-Pro-D-Trp-D-Val-D-Pro-D-Ser-D-Trp-D-Met-D-Pro-D-Pro-D-Arg-D-His-D-Thr-$NH_2$ (SEQ ID NO: 1 with an L-Dopa as Cargo or Z Group)

The procedure of the Example 1 was repeated until the coupling of the twelfth amino acid.

For the coupling the cargo (L-dopa) to the BBB-shuttle anchored onto the resin following protocol was used: the cargo-COOH (Fmoc-L-Dopa-OH) (4 eq, 800 µmols, 334 mg) in DMF (1-3 mL/g resin), PyBOP (4 eq, 800 µmols, 416 mg) and HOAt (12 eq, 2.4 mmol, 327 mg) were added sequentially to the resin followed by the addition of 12 eq of DIEA (2.4 mmol, 408 µL). The mixture was allowed to react with intermittent manual stirring for 1.5 h. The solvent was removed by suction, the resin washed with DMF (5×30 s) and DCM (5×30 s). The coupling was repeated twice under the same conditions. The extent of coupling was monitored using the p-nitro phenyl ester test. The Fmoc group was removed with a 20% solution of piperidine in DMF (v/v) using two 1 min treatments and 1 treatment of 10 minutes.

The cleavage step was performed treating the resin with a mixture of TFA (94%), $H_2O$ (2.5%), EDT (2.5%) and TIS (1%) (1×1 h). Tert-butyl methyl ether and was added to product obtained and the mixture was centrifuged (2×8 min). The supernatant was removed and the pellet resuspended in a mixture of $H_2O$ and MeCN (1:1). The product was filtered out and lyophilized.

Product characterization. Reverse phase HPLC: linear gradient from 0 to 100% MeCN in $H_2O$ in 8 minutes using a Sunfire $C_{18}$ column (100 mm×4.6 mm, 3.5 mm, 100 Å, Waters), flow of 1 mL/min; Retention time: 4.51 min. Mass spectrometry (MALDI-TOF): [M+H]+: 1670.2; Yield (synthesis and purification): 3.8%.

Example 9

Preparation of the Compound 5(6)-Carboxyfluorescein-D-Pro-D-Trp-D-Val-D-Pro-D-Ser-D-Trp-D-Met-D-Pro-D-Pro-D-Arg-D-His-D-Thr-$NH_2$ (SEQ ID NO: 1 with 5(6)-Carboxifluorescein as Cargo or Z Group)

The procedure was repeated as in Example 1 until the coupling of the twelfth amino acid.

For the coupling the cargo (5(6)-carboxyfluorescein to the BBB-shuttle anchored onto the resin following protocol was used: the cargo-COOH (5(6)-carboxyfluorescein) (4 eq, 800 µmols, 301 mg) in DMF (1-3 mL/g resin), PyBOP (4 eq, 800 µmols, 416 mg) and HOAt (12 eq, 2.4 mmol, 327 mg) were added sequentially to the resin followed by the addition of 12 eq of DIEA (2.4 mmol, 408 µL). The mixture was allowed to react with intermittent manual stirring for 1.5 h. The solvent was removed by suction, the resin washed with DMF (5×30 s) and DCM (5×30 s). The coupling was repeated twice under the same conditions. The extent of the coupling was monitored using the p-nitro phenyl ester test.

The cleavage step was performed treating the resin with a mixture of TFA (94%), $H_2O$ (2.5%), EDT (2.5%) and TIS (1%) (1×1 h). tert-butyl methyl ether was added to the obtained product, the mixture was centrifuged (2×8 min). The supernatant was removed and the pellet resuspended in a mixture of $H_2O$ and MeCN (1:1). The product was filtered out and lyophilized.

Product characterization. Reverse phase HPLC: linear gradient from 0 to 100% MeCN in $H_2O$ in 8 minutes using a Sunfire $C_{18}$ column (100 mm×4.6 mm, 3.5 mm, 100 Å, Waters), flow of 1 mL/min; Retention time: 5.06 min. Mass spectrometry (MALDI-TOF): [M+H]+: 1849.3; Yield (synthesis and purification): 4.2%.

Example 10

Preparation of Quantum Dot-Gly-D-Pro-D-Trp-D-Val-D-Pro-D-Ser-D-Trp-D-Met-D-Pro-D-Pro-D-Arg-D-His-D-Thr-$NH_2$ (SEQ ID NO: 2 with Quantum Dot as Cargo or Z Group)

The procedure was repeated as in Example 1 until the coupling of the twelfth amino acid.

In this example as a spacer between the shuttle and the cargo a molecule of glycine was used. Glycine was added to the shuttle anchored onto the resin using the following protocol: the protected amino acid (Fmoc-Gly-OH, 4 eq. 800 µmols, 190 mg), PyBOP (4 eq, 800 µmols, 416 mg), HOAt (12 eq, 2.4 mmol, 327 mg) dissolved in DMF (1-3 mL/g resin) were added sequentially to the resin, subsequently DIEA was added (12 eq, 2.4 mmol, 408 µL). The mixture was allowed to react with intermittent manual stirring for 1.5 h. The solvent was removed by suction and the resin was washed with DMF (5×30 s) and DCM (5×30 s). The coupling reaction was carried out twice under the same conditions. The extent of coupling was checked by the colorimetric p-nitro phenyl ester assay. The Fmoc group was removed with a 20% solution of piperidine in DMF (v/v) using two 1 min treatments and 1 treatment of 10 minutes.

The cleavage step of the shuttle with the spacer was performed treating the resin with a mixture of TFA (94%), $H_2O$ (2.5%), EDT (2.5%) and TIS (1%) (1×1 h). Tert-butyl methyl ether was added to the product obtained, the resulting mixture was centrifuged (2×8 min). The supernatant was removed and the pellet was resuspended in a mixture of $H_2O$ and MeCN (1:1). The product was filtered out and lyophilized.

The coupling of the shuttle equipped with the glycine spacer to the cargo (quantum dot) was performed in solution according to the following protocol: 0.01 mmol (2 mg) of N-(3-dimethylaminopropyl)-N'-etilcarbodimida and 0.025 mmol of N-hydroxysuccinimide (3 mg) were added to 4 mL of a solution of quantum dots (2 mg) in MES (50 mM, pH 6.5), the mixture was allowed to react for 30 minutes. After which 0.08 μmoles (0.12 mg) of the shuttle with spacer of glycine were added. This mixture was allowed to react for 24 h with gentle agitation. The excess peptide and unreacted reagent was removed by dialysis at 4° C. against water for 36 h. The water was changed every 12 hours.

Product characterization. The product was characterized by zeta potential measurements at pH 7.4. The product cargo-shuttle zeta displayed a potential of −33.8 mV (the quantum dots none-linked to the shuttle showed a zeta potential of −37.4 mV).

Example 11

Preparation of nanoparticle superparamagnetic iron oxide (SPION)-Gly-D-Pro-D-Trp-D-Val-D-Pro-D-Ser-D-Trp-D-Met-D-Pro-D-Pro-D-Arg-D-His-D-Thr-NH$_2$ (SEQ ID NO: 2 with SPION as Cargo or Z Group)

Example 10 was repeated until the cleavage step of the shuttle with the spacer inclusive.

The binding of the shuttle with a glycine spacer to the superparamagnetic iron oxide nanoparticle in solution was performed according to the following protocol: 0.01 mmol (2 mg) of N-(3-dimethylaminopropyl)-N'-etilcarbodiimide and 0.025 mmoles of N-hydroxysuccinimide (3 mg) were added to 4 mL of a solution of nanoparticles (2 mg) in MES (50 mM, pH 6.5), allowed to react for 30 minutes and added 0.08 μmol (0.12 mg) of shuttle glycine spacer. It was allowed to react for 24 h under gentle agitation, Excess peptide and unreacted reagent was removed by dialysis at 4° C. against water for 36 h. The water was changed every 12 hours.

Product characterization. The product was characterized by zeta potential measurements at pH 7.4. The product showed a post-shuttle potential of −31 mV Z (unbound nanoparticles to the shuttle showed a zeta potential of −37.1 mV).

Example 12

Preparation of H-D-Ala-D-NMePhe-D-Nal(2)-D-Val-D-Leu-D-Lys-D-Lys-D-Pro-D-Trp-D-Val-D-Pro-D-Ser-D-Trp-D-Met-D-Pro-D-Pro-D-Arg-D-His-D-Thr-NH$_2$ (SEQ ID NO: 1 with SEQ ID NO: 3 as Cargo or Z Group)

The procedure was repeated as in Example 1 until the coupling of the twelfth amino acid.

In this example the cargo was synthesized by solid-phase synthesis directly on the shuttle anchored onto the resin. The first protected amino acid derivative of the cargo was coupled to the BBB-shuttle anchored onto the resin using the following protocol: the protected amino acid (Fmoc-D-Lys (Boc)-OH, 4 eq. 800 μmols, 375 mg), PyBOP (4 eq, 800 μmols, 416 mg), HOAt (12 eq, 2.4 mmol, 327 mg) dissolved in DMF (1-3 mL/g resin) were added sequentially to the resin, subsequently DIEA was added (12 eq, 2.4 mmol, 408 μL). The mixture was allowed to react with intermittent manual stirring for 1.5 h. The solvent was removed by suction and the resin was washed with DMF (5×30 s) and DCM (5×30 s). The coupling reaction was repeated twice under the same conditions. The extent of coupling was checked using the colorimetric assay of p-nitro phenyl ester. The Fmoc group was removed with a 20% solution of piperidine in DMF (v/v) using two 1 min treatments a 1 treatment of 10 minutes.

The protected amino acid derivative of the second position of the cargo was coupled over the first amino acid of the cargo anchored onto the resin using the following protocol: the protected amino acid (Fmoc-D-Lys(Boc)-OH, 4 eq. 800 μmols, 375 mg) and TBTU (4 eq, 800 μmols, 257 mg) dissolved in DMF (1-3 mL/g resin) were sequentially added to the resin, subsequently DIEA was added (8 eq, 1.3 mmol, 267 μL). The mixture was allowed to react with intermittent manual stirring for 1.5 h. The solvent was removed by suction and the resin was washed with DMF (5×30 s) and DCM (5×30 s). The extent of coupling was checked by the Kaiser colorimetric assay. The Fmoc group was removed with a 20% solution of piperidine in DMF (v/v) using two 1 min treatments and 1 treatment of 10 minutes.

The protected amino acid derivative of the third position of the cargo was coupled to the second amino acid of the cargo anchored onto the resin using the following protocol: the protected amino acid (Fmoc-D-Leu-OH, 4 eq. 800 μmols, 283 mg) and TBTU (4 eq, 800 μmols, 257 mg) dissolved in DMF (1-3 mL/g resin) were added sequentially to the resin, subsequently DIEA was added (8 eq, 1.3 mmol, 267 μL). The mixture was allowed to react with intermittent manual stirring for 1.5 h. The solvent was removed by suction and the resin was washed with DMF (5×30 s) and DCM (5×30 s). The extent of coupling was checked by the Kaiser colorimetric assay. The Fmoc group was removed with a 20% solution of piperidine in DMF (v/v) using two 1 min treatments and 1 treatment of 10 minutes.

The protected amino acid derivative of the position fourth of the cargo was coupled to the third amino acid position of the cargo anchored onto the resin using the following protocol: the protected amino acid (Fmoc-D-Val-OH, 4 eq. 800 μmols, 271 mg) and TBTU (4 eq, 800 μmols, 257 mg) dissolved in DMF (1-3 mL/g resin) were added sequentially to the resin, subsequently DIEA was added (8 eq, 1.3 mmol, 267 μL). The mixture was allowed to react with intermittent manual stirring for 1.5 h. The solvent was removed by suction and the resin was washed with DMF (5×30 s) and DCM (5×30 s). The extent of coupling was checked by the Kaiser colorimetric assay. The Fmoc group was removed with a 20% solution of piperidine in DMF (v/v) using two 1 min treatments and 1 treatment of 10 minutes.

The protected amino acid derivative of the position of the fifth of the cargo was coupled to the fourth amino of the cargo anchored onto the resin using the following protocol: the protected amino acid (Fmoc-D-Nal(2)-OH, 4 eq. 800 μmols, 350 mg) and TBTU (4 eq, 800 μmols, 257 mg) dissolved in DMF (1-3 mL/g resin) were added sequentially to the resin, subsequently DIEA was added (8 eq, 1.3 mmol, 267 mL). The mixture was allowed to react with intermittent manual stirring for 1.5 h. The solvent was removed by suction and the resin was washed with DMF (5×30 s) and DCM (5×30 s). The extent of coupling was checked by the Kaiser colorimetric assay. The Fmoc group was removed with a 20% solution of piperidine in DMF (v/v) using two 1 min treatments and 1 treatment of 10 minutes.

The protected amino acid derivative of the sixth position of the cargo was coupled to the fifth amino acid of the cargo anchored onto the resin using the following protocol: the protected amino acid (Fmoc-D-NMePhe-OH, 4 eq. 800 µmols, 321 mg) and TBTU (4 eq, 800 µmols, 257 mg) dissolved in DMF (1-3 mL/g resin) were added sequentially to the resin, subsequently DIEA was added (8 eq, 1.3 mmol, 267 µL). The mixture was allowed to react with intermittent manual stirring for 1.5 h. The solvent was removed by suction and the resin washed with DMF (5×30 s) and DCM (5×30 s). The extent of coupling was checked by the Kaiser colorimetric assay. The Fmoc group was removed with a 20% solution of piperidine in DMF (v/v) using two 1 min treatments and 1 treatment of 10 minutes, and treatment with DBU, toluene, piperidine, DMF (5%, 5%, 20%, 70%) (2×5 min) to assess the removal of the Fmoc group.

The protected amino acid derivative of the position of the seventh of the cargo was coupled to the sixth amino acid of the cargo anchored to the resin using the following protocol: the protected amino acid (Fmoc-D-Ala-OH, 4 eq. 800 µmols, 249 mg), PyBOP (4 eq, 800 µmols, 416 mg), HOAt (12 eq, 2.4 mmol, 327 mg) dissolved in DMF (1-3 mL/g resin) were added sequentially to the resin, subsequently DIEA was added (12 eq, 2.4 mmol, 408 µL). The mixture was allowed to react with intermittent manual stirring for 1.5 h. The solvent was removed by suction and the resin was washed with DMF (5×30 s) and DCM (5×30 s). The coupling reaction was carried out twice under the same conditions. The extent of coupling was checked by the p-nitro phenyl ester colorimetric assay. The Fmoc group was removed with a 20% solution of piperidine in DMF (v/v) using two 1 min treatments and 1 treatment of 10 minutes.

The cleavage step of the cargo-shuttle construct was performed treating the resin with a mixture of TFA (94%), $H_2O$ (2.5%), EDT (2.5%) and TIS (1%) (1×1 h). Tert-butylmethyl ether was added to the product obtained and the mixture was centrifuged (2×8 min). The supernatant was removed and the pellet resuspended in a mixture of H2O and MeCN (1:1). The product was filtered out and lyophilized.

Characterization of the cargo-shuttle construct. Reverse phase HPLC: linear gradient from 0 to 100% MeCN in H2O in 8 minutes using a Sunfire $C_{18}$ column (100 mm×4.6 mm, 3.5 mm, 100 Å, Waters), flow of 1 mL/min; Retention time: 4.52 min. Mass spectrometry (MALDI-TOF): [M+H]+: 2387.3; Yield (synthesis and purification): 9.5%.

Example 13

Preparation of H-Gly-D-Pro-D-Trp-D-Val-D-Pro-D-Ser-D-Trp-D-Met-D-Pro-D-Pro-D-Arg-D-His-D-Thr-Antibody (SEQ ID NO: 2 with an Antibody as Cargo or Z Group) Using Tech 1

Example 3 was repeated until the cleavage step. The binding of the shuttle with the antibody was done following aminooxy tech 1, in solution was performed according to the following protocol: 25 µL of BvW ($3.3 \cdot 10^{-9}$ mol, $5.0 \cdot 10^{-4}$ g) was diluted with 75 µL of phosphate buffer 25 mM pH 6.5. Pyridoxal 5'-phosphate (PLP) (298 eq, $1.0 \cdot 10^{-7}$ mol, $2.5 \cdot 10^{-5}$ g) was dissolved in 100 µL of phosphate buffer 25 mM and the pH was made up to 6.5 with 1 M HCl. The BvW solution was mixed with the PLP solution and incubated at 20° C. for 48 h. A Nap-5 size exclusion column was used to separate the excess small molecules from the derivatized antibody using phosphate buffer 25 mM pH 6.2. The antibody was concentrated to 100 µL using a Vivaspin 500 with 50 kDa MWCO and washed twice with phosphate buffer 25 mM pH 6.2. The H-Gly-D-Pro-D-Trp-D-Val-D-Pro-D-Ser-D-Trp-D-Met-D-Pro-D-Pro-D-Arg-D-His-D-Thr-aminooxy (60 eq, $2.0 \cdot 10^{-7}$ mol) was dissolved in 50 µL of phosphate buffer 25 mM and the pH was made up to 6.2 with 1 M aqueous HCl. The transaminated antibody from the Nap-5 column were mixed with the peptide solution and with 50 µL of a $4.10^{-3}$ M solution of aniline (60 eq, $2.0 \cdot 10^{-7}$ mol, $1.9 \cdot 10^{-5}$ g); the mixture was left to react for 48 h. Excess reagents were removed using a Nap-5 size-exclusion column with phosphate buffer 25 mM pH 6.2.

The conjugates were characterized by MALDI-TOF MS and the amount of peptide was quantified using 3 cycles of Edman sequencing (1-2 peptides/Ab).

Example 14

Preparation of H-Gly-D-Pro-D-Trp-D-Val-D-Pro-D-Ser-D-Trp-D-Met-D-Pro-D-Pro-D-Arg-D-His-D-Thr-Antibody (SEQ ID NO: 2 with an Antibody as Cargo or Z Group) Using Tech 2

Example 3 was repeated until the cleavage step. The binding of the shuttle with the antibody was done following aminooxy tech 2, in solution was performed according to the following protocol: 25 µL of BvW ($3.3 \cdot 10^{-9}$ mol, $5.0 \cdot 10^{-4}$ g) was diluted with 75 µL of PBS pH 7.2 and mixed with 10 µL of 0.1 M NaIO4 in water (54 eq, $1.0 \cdot 10^{-6}$ mol, $2.1 \cdot 10^{-4}$ g). The mixture was left to react 2 h at 4° C. preserved from light. A Nap-5 size exclusion column was used to separate the excess small molecules from the derivatized antibody using phosphate buffer 50 mM pH 6.2. H-Gly-D-Pro-D-Trp-D-Val-D-Pro-D-Ser-D-Trp-D-Met-D-Pro-D-Pro-D-Arg-D-His-D-Thr-aminooxy (60 eq, $2.0 \cdot 10^{-7}$ mol, $3.4 \cdot 10^{-4}$ g) was dissolved in 50 µL of phosphate buffer 25 mM and the pH was made up to 6.2 with 1 M aqueous HCl. The transaminated antibody from the Nap-5 column were mixed with the peptide solution and with 50 µL of a $4.10^{-3}$ M solution of aniline (60 eq, $2.0 \cdot 10^{-7}$ mol, $1.9 \cdot 10^{-5}$ g); the mixture was left to react for 48 h. Excess reagents were removed using a Nap-5 size-exclusion column with phosphate buffer 25 mM pH 6.2.

The conjugates were characterized by MALDI-TOF MS (1-2 peptides/Ab).

Example 15

Preparation of 5(6)-Carboxyfluorescein-L-Lys(Antibody)-D-Pro-D-Trp-D-Val-D-Pro-D-Ser-D-Trp-D-Met-D-Pro-D-Pro-D-Arg-D-His-D-Thr-$NH_2$ (SEQ ID NO: 1 with 5(6)-Carboxifluorescein and an Antibody as Cargos or Z Groups in the Compound of Formula (II)) Using Tech 3

Example 7 was repeated until the cleavage step. The binding of the shuttle with the antibody was done following maleimido tech 3, in solution was performed according to the following protocol: 25 µL of BvW ($3.3 \cdot 10^{-9}$ mol, $5.0 \cdot 10^{-4}$ g) was diluted with 75 µL of PBS pH 7.2 and incubated with 2-iminothiolane (30 eq, $1.0 \cdot 10^{-7}$ mol, $1.4 \cdot 10^{-5}$ g) for 1 h at 20° C. A Nap-5 size exclusion column was used to separate the non-reacted 2-iminothiolane from the thiolated antibody using PBS pH 7.2. carboxyfluorescein-L-Lys(maleimide)-D-Pro-D-Trp-D-Val-D-Pro-D-Ser-D-Trp-D-Met-D-Pro-D-Pro-D-Arg-D-His-D-Thr-NH$_2$ (10 eq, 3.3·10$^{-8}$ mol, 7.2·10$^{-5}$ g) was dissolved in 50 µL of PBS and mixed with the oxidized antibody. The mixture is left to react for 2 h at 20° C. Excess peptide is removed using a Nap-5 size-exclusion column using PBS pH 7.2.

The conjugates are characterized by MALDI-TOF MS and by gel electrophoresis. (2 peptides/Ab)

Example 16

Preparation of 5(6)-Carboxifluorescein-L-Lys(Antibody)-D-Pro-D-Trp-D-Val-D-Pro-D-Ser-D-Trp-D-Met-D-Pro-D-Pro-D-Arg-D-His-D-Thr-NH$_2$ (SEQ ID NO: 1 with 5(6)-Carboxifluorescein and an Antibody as Cargos or Z Groups in the Compound of Formula (II)) Using Tech 4.1.A and 4.3

Example 7 was repeated until the cleavage step. The binding of the shuttle to the antibody was done following maleimido technology tech 4.

An antibody solution (1 mgmL$^{-1}$, 500 µL) was partially reduced by DTT (3.25 eq, 2.2 µL, 10 mM) or TCEP (2.75 eq, 1.8 µL, 10 mM) in 0.025 M sodium borate pH 8, 0.025 M NaCl, 1 mM EDTA for 2 h at 37° C. The excess of DTT was purified away from the partially reduced antibody by size exclusion (Nap 5, GE Healthcare following manufacturer instructions). The concentration of antibody-cysteine thiols produced was determined by titrating with DTNB, typically resulting in 3.0 to 4.0 thiols/antibody.

Partially reduced antibody was alkylated with 1.1 molar equiv of 5(6)-carboxifluorescein-L-Lys(maleimido)-D-Pro-D-Trp-D-Val-D-Pro-D-Ser-D-Trp-D-Met-D-Pro-D-Pro-D-Arg-D-His-D-Thr-NH$_2$/antibody-cysteine thiol (4 eq, 5.8 µL, 10 mgmL$^{-1}$ DMSO) The alkylation reaction was performed at 0° C. for 30 min. Cysteine (1 mM final) was used to quench any unreacted, excess of 5(6)-carboxifluorescein-L-Lys(maleimido)-D-Pro-D-Trp-D-Val-D-Pro-D-Ser-D-Trp-D-Met-D-Pro-D-Pro-D-Arg-D-His-D-Thr-NH$_2$. The excess of peptide was removed from the partially reduced antibody by size exclusion (Nap 5, GE Healthcare following manufacturer instructions).

The antibody concentration was quantified using Nanodrop (coef ext molar=222714 M$^{-1}$ cm$^{-1}$).

Product characterization. The product was characterized by MALDI-TOF. MS: 25827; SDS page and LC MS (1 to 3 peptides/Ab).

Example 17

Preparation of Rhodamine b-L-Lys(Antibody)-D-Pro-D-Trp-D-Val-D-Pro-D-Ser-D-Trp-D-Met-D-Pro-D-Pro-D-Arg-D-His-D-Thr-NH$_2$ (SEQ ID NO: 1 with Rhodamine b and an Antibody as Cargos or Z Groups in the Compound of Formula (II)) Using Tech 3

Example 6 was repeated until the cleavage step. The binding of the shuttle with the antibody was done following maleimido tech 3, in solution was performed according to the following protocol: 25 µL of BvW (3.3·10$^{-9}$ mol, 5.0·10$^4$ g) was diluted with 75 µL of PBS pH 7.2 and incubated with 2-iminothiolane (30 eq, 1.0·10$^{-7}$ mol, 1.4·10$^{-5}$ g) for 1 h at 20° C. A Nap-5 size exclusion column was used to separate the non-reacted 2-iminothiolane from the thiolated antibody using PBS pH 7.2. rhodamine b-L-Lys(maleimide)-D-Pro-D-Trp-D-Val-D-Pro-D-Ser-D-Trp-D-Met-D-Pro-D-Pro-D-Arg-D-His-D-Thr-NH$_2$ (10 eq, 3.3·10$^{-8}$ mol, 7.4·10$^{-5}$ g) was dissolved in 50 µL of PBS and mixed with the oxidized antibody. The mixture is left to react for 2 h at 20° C. Excess peptide is removed using a Nap-5 size-exclusion column using PBS pH 7.2.

The conjugates are characterized by MALDI-TOF MS and by gel electrophoresis. (5 peptides/Ab)

Example 18

Preparation of Rhodamine b-L-Lys(Antibody)-D-Pro-D-Trp-D-Val-D-Pro-D-Ser-D-Trp-D-Met-D-Pro-D-Pro-D-Arg-D-His-D-Thr-NH$_2$ (SEQ ID NO: 1 with Rhodamine b and an Antibody as Cargos or Z Groups in the Compound of Formula (II)) Using Tech 4.1.A and 4.3

Example 6 was repeated until the cleavage step. The binding of the shuttle with the antibody was done following maleimido technology tech 4. An antibody solution (1 mgmL$^{-1}$, 500 µL) was partially reduced by DTT (3.25 eq, 2.2 µL, 10 mM) or TCEP (2.75 eq, 1.8 µL, 10 mM) in 0.025 M sodium borate pH 8, 0.025 M NaCl, 1 mM EDTA for 2 h at 37° C. The excess of DTT was purified away from the partially reduced antibody by size exclusion (Nap 5, GE Healthcare following manufacturer instructions). The concentration of antibody-cysteine thiols produced was determined by titrating with DTNB, typically resulting in 3.0 to 4.0 thiols/antibody.

Partially reduced antibody was alkylated with 1.1 molar equiv rhodamine b-L-Lys(maleimido)-D-Pro-D-Trp-D-Val-D-Pro-D-Ser-D-Trp-D-Met-D-Pro-D-Pro-D-Arg-D-His-D-Thr-NH$_2$/antibody-cysteine thiol (4 eq, 5.8 µL, 10 mgmL$^{-1}$ DMSO) The alkylation reaction was performed at 0° C. for 30 min. Cysteine (1 mM final) was used to quench any unreacted, excess of rhodamine b-L-Lys(maleimido)-D-Pro-D-Trp-D-Val-D-Pro-D-Ser-D-Trp-D-Met-D-Pro-D-Pro-D-Arg-D-His-D-Thr-NH$_2$. The excess of peptide was removed from the partially reduced antibody by size exclusion (Nap 5, GE Healthcare following manufacturer instructions).

The antibody concentration was quantified using Nanodrop (coef ext molar=222714 M$^{-1}$ cm$^{-1}$).

Product characterization. The product was characterized by MALDI-TOF. MS: 25827; SDS page and LC MS (2 to 3 peptides/Ab).

Example 19

Preparation of Rhodamine b-L-Lys(Antibody)-D-Pro-D-Trp-D-Val-D-Pro-D-Ser-D-Trp-D-Met-D-Pro-D-Pro-D-Arg-D-His-D-Thr-NH$_2$ (SEQ ID NO: 1 with Rhodamine b and an Antibody as Cargos or Z Groups in the Compound of Formula (II)) Using Tech 4.1.B and 4.3

Example 6 was repeated until the cleavage step. The binding of the shuttle with the antibody was done following maleimido technology tech 4. An antibody solution (1 mgmL$^{-1}$, 500 µL) was partially reduced by TCEP (2.75 eq, 1.8 µL, 10 mM) in 0.025 M sodium borate pH 8, 0.025 M NaCl, 1 mM EDTA for 2 h at 37° C. The concentration of antibody-cysteine thiols produced was determined by titrating with DTNB, typically resulting in 3.5 to 4.0 thiols/antibody.

Partially reduced antibody was alkylated with 1.1 molar equiv rhodamine b-L-Lys(maleimido)-D-Pro-D-Trp-D-Val-D-Pro-D-Ser-D-Trp-D-Met-D-Pro-D-Pro-D-Arg-D-His-D-Thr-NH$_2$/antibody-cysteine thiol (4 eq, 5.8 µL, 10 mgmL$^{-1}$ DMSO) The alkylation reaction was performed at 0° C. for 30 min. Cysteine (1 mM final) was used to quench any unreacted, excess of rhodamine b-L-Lys(maleimido)-D-Pro-D-Trp-D-Val-D-Pro-D-Ser-D-Trp-D-Met-D-Pro-D-Pro-D-Arg-D-His-D-Thr-NH$_2$. The excess of peptide was removed from the partially reduced antibody by size exclusion (Nap 5, GE Healthcare following manufacturer instructions).

The antibody concentration was quantified using Nanodrop (coef ext molar=222714 M$^{-1}$ cm$^{-1}$).

Product characterization. The product was characterized by MALDI-TOF. MS: 150707-155257; SDS page and LC MS (2 to 3 peptides/Ab).

Example 20

Preparation of Rhodamine b-L-Lys(Antibody)-D-Pro-D-Trp-D-Val-D-Pro-D-Ser-D-Trp-D-Met-D-Pro-D-Pro-D-Arg-D-His-D-Thr-NH$_2$ (SEQ ID NO: 1) with Rhodamine b and an Antibody as Cargos or Z Groups in the Compound of Formula (II)) Using Tech 4.2 and 4.3

Example 6 was repeated until the cleavage step. The binding of the shuttle with the antibody was done following maleimido technology tech 4.

An antibody solution (2.8 mgmL$^{-1}$, 500 µL) was totally reduced by DTT (150 is eq) in 0.025 M sodium borate pH 8, 0.025 M NaCl, 1 mM EDTA for 2 h at 37° C. The excess of DTT was purified away from the partially reduced antibody by size exclusion (Nap 5, GE Healthcare following manufacturer instructions). The fully reduced antibody was cooled to 0° C. and then treated with 2.0 equivalents of DTNB (1.85 µL, 4 mgmL$^{-1}$, 0° C., 20 min). Without further purification the antibody was alkylated with 1.1 molar equiv rhodamine b-L-Lys(maleimido)-D-Pro-D-Trp-D-Val-D-Pro-D-Ser-D-Trp-D-Met-D-Pro-D-Pro-D-Arg-D-His-D-Thr-NH$_2$/antibody-cysteine thiol (9 eq, 18 µL, 10 mgmL$^{-1}$ DMSO) The alkylation reaction was performed at 0° C. for 30 min. Cysteine (1 mM final) was used to quench any unreacted, excess of rhodamine b-L-Lys(maleimido)-D-Pro-D-Trp-D-Val-D-Pro-D-Ser-D-Trp-D-Met-D-Pro-D-Pro-D-Arg-D-His-D-Thr-NH$_2$. The excess of peptide was removed from the partially reduced antibody by size exclusion (Nap 5, GE Healthcare following manufacturer instructions).

The antibody concentration was quantified using Nanodrop (coef ext molar=222714 M$^{-1}$ cm$^{-1}$).

Product characterization. The product was characterized by MALDI-TOF. MS: 167061.9; SDS page and LC MS (8 peptides/Ab).

Comparative Example 1

Preparation of H-L-Thr-L-His-L-Arg-Pro-L-L-Pro-L-Met-L-Trp-L-Ser-Pro-L-L-Val-L-Trp-L-Pro-NH$_2$ (SEQ ID NO: 5)

The synthesis was performed in a scale 200 µmol. For the coupling of the first amino acid onto the Fmoc-Rink amide p-MBHA resin the following protocol was used: the first protected amino acid (Fmoc-L-Pro-OH, 4 eq. 800 µmols, 270 mg), TBTU (4 eq, 800 µmols, 257 mg) dissolved in DMF (1-3 mL/g resin) were added sequentially to the resin, subsequently DIEA was added (8 eq, 1.3 mmol, 267 microL). The mixture was allowed to react with intermittent manual stirring for 1.5 h. The solvent was removed by suction and the resin washed with DMF (5×30 s) and DCM (5×30 s). The extent of coupling was checked by the Kaiser colorimetric assay. The Fmoc group was removed with a 20% solution of piperidine in DMF (v/v) using two 1 min treatments and 1 treatment of 10 minutes, and treatment with DBU, toluene, piperidine, DMF (5%, 5%, 20%, 70%) (2×5 min) to assess the removal of the Fmoc group.

The protected amino acid derivative of the second amino acid was coupled to the first amino acid anchored onto the resin using the following protocol: the protected amino acid (Fmoc-L-Trp(Boc)-OH, 4 eq. 800 µmols, 421 mg), PyBOP (4 eq, 800 µmols, 416 mg), HOAt (12 eq, 2.4 mmol, 327 mg) dissolved in DMF (1-3 mL/g resin) were added sequentially to the resin, subsequently DIEA was added (12 eq, 2.4 mmol, 408 µL). The mixture was allowed to react with intermittent manual stirring for 1.5 h. The solvent was removed by suction and the resin washed with DMF (5×30 s) and DCM (5×30 s). The coupling reaction was carried out twice under the same conditions. The extent of coupling was checked by the colorimetric assay of p-nitro phenyl ester. The Fmoc group was removed with a 20% solution of piperidine in DMF (v/v) using two 1 min treatments and 1 treatment of 10 minutes.

The third amino acid protected derivative was coupled to the second amino acid already anchored to the resin using the following protocol: the protected amino acid (Fmoc-L-Val-OH, 4 eq, 800 µmols, 271 mg) and the coupling agent TBTU (4 eq, 800 µmols, 257 mg) dissolved in DMF (1-3 mL/g resin) were added sequentially to the resin followed by addition of DIEA (8 eq, 1.3 mmol, 267 µL). The mixture was allowed to react with intermittent manual stirring for 1.5 h. The solvent was removed by suction and the resin washed with DMF (5×30 s) and DCM (5×30 s). The extent of coupling was checked by the Kaiser colorimetric assay. The Fmoc group was removed with a 20% solution of piperidine in DMF (v/v) using two 1 min treatments and 1 treatment of 10 minutes.

The protected amino acid derivative of the fourth amino acid was coupled to the third amino acid anchored onto the resin using the following protocol: the protected amino acid (Fmoc-L-Pro-OH, 4 eq. 800 µmols, 270 mg), TBTU (4 eq, 800 µmols, 257 mg) dissolved in DMF (1-3 mL/g resin) were added sequentially to the resin, subsequently DIEA was added (8 eq, 1.3 mmol, 267 µL). The mixture was allowed to react with intermittent manual stirring for 1.5 h. The solvent was removed by suction and the resin washed with DMF (5×30 s) and DCM (5×30 s). The extent of coupling was checked by the Kaiser colorimetric assay. The Fmoc group was removed with a 20% solution of piperidine in DMF (v/v) using two 1 min treatments and 1 treatment of 10 minutes, and treatment with DBU, toluene, piperidine, DMF (5%, 5%, 20%, 70%) (2×5 min) to assess the removal of the Fmoc group.

The protected amino acid derivative of the fifth amino acid was coupled to the fourth amino acid anchored onto the resin using the following protocol: the protected amino acid (Fmoc-L-Ser(tBu)-OH, 4 eq. 800 µmols, 307 mg), PyBOP (4 eq, 800 µmols, 416 mg), HOAt (12 eq, 2.4 mmol, 327 mg) dissolved in DMF (1-3 mL/g resin) were added sequentially to the resin, subsequently DIEA was added (12 eq, 2.4 mmol, 408 µL). The mixture was allowed to react with intermittent manual stirring for 1.5 h. The solvent was removed by suction and the resin washed with DMF (5×30 s) and DCM (5×30 s). The coupling reaction was carried out twice under the same conditions. The extent of coupling was checked by the colorimetric p-nitro phenyl ester assay. The Fmoc group was removed with a 20% solution of piperidine in DMF (v/v) using two 1 min treatments and 1 treatment of 10 minutes, and treatment with DBU, toluene, piperidine, DMF (5%, 5%, 20%, 70%) (2×5 min) to assess the removal of the Fmoc group.

The protected amino acid derivative of the sixth amino acid was coupled to the fifth amino acid anchored onto the resin using the following protocol: the protected amino acid (Fmoc-L-Trp(Boc)-OH, 4 eq. 800 µmols, 421 mg), TBTU (4 eq. 800 µmols, 257 mg) dissolved in DMF (1-3 mL/g resin) were added sequentially to the resin, subsequently DIEA was added (8 eq, 1.3 mmol, 267 µL). The mixture was allowed to react with intermittent manual stirring for 1.5 h. The solvent was removed by suction and the resin washed with DMF (5×30 s) and DCM (5×30 s). The extent of coupling was checked by the Kaiser colorimetric assay. The Fmoc group was removed with a 20% solution of piperidine in DMF (v/v) using two 1 min treatments and 1 treatment of 10 minutes.

The protected amino acid derivative of the seventh amino acid was coupled to the sixth amino acid anchored onto the resin using the following protocol: the protected amino acid (Fmoc-L-Met-OH, 4 eq. 800 µmols, 297 mg), TBTU (4 eq, 800 µmols, 257 mg) dissolved in DMF (1-3 mL/g resin) were added sequentially to the resin, subsequently DIEA was added (8 eq, 1.3 mmol, 267 µL). The mixture was allowed to react with intermittent manual stirring for 1.5 h. The solvent was removed by suction and the resin washed with DMF (5×30 s) and DCM (5×30 s). The extent of coupling was checked by the Kaiser colorimetric assay. The Fmoc group was removed with a 20% solution of piperidine in DMF (v/v) using two 1 min treatments and 1 treatment of 10 minutes.

The protected amino acid derivative of the eighth amino acid is coupled to the seventh amino acid anchored onto the resin using the following protocol: the protected amino acid (Fmoc-L-Pro-OH, 4 eq. 800 µmols, 270 mg), TBTU (4 eq, 800 µmols, 257 mg) dissolved in DMF (1-3 mL/g resin) were added sequentially to the resin, subsequently DIEA was added (8 eq, 1.3 mmol, 267 µL). The mixture was allowed to react with intermittent manual stirring for 1.5 h. The solvent was removed by suction and the resin washed with DMF (5×30 s) and DCM (5×30 s). The extent of coupling was checked by the Kaiser colorimetric assay. The Fmoc group was removed with a 20% solution of piperidine in DMF (v/v) using two 1 min treatments and 1 treatment of 10 minutes, and treatment with DBU, toluene, piperidine, DMF (5%, 5%, 20%, 70%) (2×5 min) to assess the removal of the Fmoc group.

The protected amino acid derivative of the ninth amino acid was coupled to the eighth amino acid anchored onto the resin using the following protocol: the protected amino acid (Fmoc-L-Pro-OH, 4 eq. 800 µmols, 270 mg), PyBOP (4 eq, 800 µmols, 416 mg), HOAt (12 eq, 2.4 mmol, 327 mg) dissolved in DMF (1-3 mL/g resin) were added sequentially to the resin, subsequently DIEA was added (12 eq, 2.4 mmol, 408 µL). The mixture was allowed to react with intermittent manual stirring for 1.5 h. The solvent was removed by suction and the resin washed with DMF (5×30 s) and DCM (5×30 s). The coupling reaction was carried out twice under the same conditions. The extent of coupling was checked by the colorimetric p-nitro phenyl ester assay. The Fmoc group was removed with a 20% solution of piperidine in DMF (v/v) using two 1 min treatments and 1 treatment of 10 minutes, and treatment with DBU, toluene, piperidine, DMF (5%, 5%, 20%, 70%) (2×5 min) to assess the removal of the Fmoc group.

The protected amino acid derivative of the tenth amino acid was coupled to the ninth amino acid anchored onto the resin using the following protocol: the protected amino acid (Fmoc-L-Arg (Pbf)-OH, 4 eq. 800 µmols, 519 mg), PyBOP (4 eq, 800 µmols, 416 mg), HOAt (12 eq, 2.4 mmol, 327 mg) dissolved in DMF (1-3 mL/g resin) were added sequentially to the resin, subsequently DIEA was added (12 eq, 2.4 mmol, 408 microL). The mixture was allowed to react with intermittent manual stirring for 1.5 h. The solvent was removed by suction and the resin washed with DMF (5×30 s) and DCM (5×30 s). The coupling reaction was carried out twice under the same conditions. The extent of coupling was checked by the colorimetric p-nitro phenyl ester assay. The Fmoc group was removed with a 20% solution of piperidine in DMF (v/v) using two 1 min treatments and 1 treatment of 10 minutes.

The protected amino acid derivative of the eleventh amino acid was coupled to the tenth amino acid already anchored to the resin using the following protocol: the protected amino acid (Fmoc-L-His(Trt)-OH, 4 eq. 800 µmols, 496 mg), TBTU (4 eq, 800 µmols, 257 mg) dissolved in DMF (1-3 mL/g resin) were added sequentially to the resin, subsequently DIEA was added (8 eq, 1.3 mmol, 267 µL). The mixture was allowed to react with intermittent manual stirring for 1.5 h. The solvent was removed by suction and the resin washed with DMF (5×30 s) and DCM (5×30 s). The extent of coupling was checked by the Kaiser colorimetric assay. The Fmoc group was removed with a 20% solution of piperidine in DMF (v/v) using two 1 min treatments a 1 treatment of 10 minutes.

The protected amino acid derivative of the twelfth amino acid was coupled to the eleventh amino acid anchored onto the resin using the following protocol: the protected amino acid (Fmoc-L-Thr (tBu)-OH, 4 eq. 800 µmols, 257 mg), TBTU (4 eq, 800 µmols, 257 mg) dissolved in DMF (1-3 mL/g resin) were added sequentially to the resin, subsequently DIEA was added (8 eq, 1.3 mmol, 267 µL). The mixture was allowed to react with intermittent manual stirring for 1.5 h. The solvent was removed by suction and the resin washed with DMF (5×30 s) and DCM (5×30 s). The extent of coupling was checked by the Kaiser colorimetric assay. The Fmoc group was removed with a 20% solution of piperidine in DMF (v/v) using two 1 min treatments and 1 treatment of 10 minutes.

The cleavage step was performed treating the resin with a mixture of TFA (94%), $H_2O$ (2.5%), EDT (2.5%) and TIS (1%) (1×1 h). tert-butyl methyl ether was added to the product obtained and the mixture was centrifuged (2×8 min). The supernatant was removed and the pellet resuspended in a mixture of $H_2O$ and MeCN (1:1). The product was filtered out and lyophilized.

Product characterization. Reverse phase HPLC: linear gradient from 0 to 100% MeCN in $H_2O$ in 8 minutes using a Sunfire $C_{18}$ column (100 mm×4.6 mm, 3.5 mm, 100 Å, Waters), flow of 1 mL/min; Retention time: 4.95 min. Mass spectrometry (MALDI-TOF): [M+H]+: 1489.6; Yield (synthesis and purification): 12%.

Comparative Example 2

Preparation of H-D-Thr-D-His-D-Arg-D-Pro-D-Pro-D-Met-D-Trp-D-Ser-D-Pro-D-Val-D-Trp-D-Pro-NH$_2$ (SEQ ID NO: 6)

Comparative Example 1 was repeated but using the corresponding D-amino acids instead of L-amino acids.

Product characterization. Reverse phase HPLC: linear gradient from 0 to 100% MeCN in $H_2O$ in 8 minutes using a Sunfire $C_{18}$ column (100 mm×4.6 mm, 3.5 mm, 100 Å, Waters), flow of 1 mL/min; Time retention: 4.3 min. Mass spectrometry (MALDI-TOF): [M+H]+: 1489.6; Yield (synthesis and purification): 9.8%.

Example 21

Evaluation of Transport Across the BBB Using an In Vitro Cell Assay

The evaluation method chosen to test the compounds of formula (I) and (II) of the invention was a cell-based assay consisting of a co-culture of brain endothelial cells and astrocytes, which allows to evaluate or to predict the transport of compounds through the BBB. The co-culture method used was described by Gaillard and de Boer in 2008 (Gaillard, P J et al. "2B-Trans technology: targeted drug delivery across the blood-brain barrier" Methods *Mol Biol* 2008, vol. 437 pp. 161-175) and consists in seeding of rat astrocytes in one side of a polycarbonate filter (transwell) and the seeding of bovine brain endothelial cells on the other side of the filter. Under these conditions endothelial cells are able to reach the confluence mimicking the BBB. The system allows studying the transport of compounds that can cross the BBB by a passive transport mechanism and/or active. Is commonly used model for permeation studies and toxicity of compounds across the BBB.

The co-culture assay was used to determine the capacity of the constructs cargo-shuttle to cross the BBB. The apparent permeability of the compounds was measured in triplicate at a concentration of 50 μM for Examples 1, 2, 3, 4 and 7, and at a concentration of 0.75 nM (referred to the particle concentration) for Examples 5 and 6. All the assays were performed with transendothelial electrical resistance values equal or higher than 125 Ω·cm2 and were carried out in the presence of lucifer yellow to assess the integrity of the cell membrane during the test. The permeability tests were performed in Ringer-HEPES buffer at pH 7.4. The compound of interest was dissolved in the buffer to the desired concentration.

Once the endothelial cells were confluent on the filters (transwells) these were washed with Ringer-HEPES buffer. The acceptor well was filled with 800 μL of Ringer-HEPES buffer and the donor well with 200 μL of the solution of the compound to be studied. The system was incubated at 37° C. and 5% CO2 for 2 h. After that time the content of the acceptor and donor compartments were analyzed by HPLC, ICP or fluorescence measurements (depending on cargo anchored to the shuttle). Transport was also confirmed by mass spectrometry MALDI-TOF.

The apparent permeability was calculated using the following equation:

$$Papp = (dQ/dt)*(1/A)*(1/C0) \, (cm/s)$$

Where (dQ/dt) is the amount of compound present in the compartment acceptor function of time (nmol/s). A is the area of the filter (cm2) and C0 is the initial concentration of the compound applied in the donor compartment (nmol/mL).

In Table 2 it can be observed how the use of the shuttle-cargo construct allows that cargos that do not cross themselves are able to do so by means of the BBB-shuttle. Being the shuttle of the example 1 notably more effective than the comparative example 1 with L-amino acids or than the comparative example 2 with D-amino acids. The retro-enantio version with D-amino acids has a surprisingly high transport through the blood-brain barrier.

TABLE 2

Apparent permeability (Papp) and percentage of transport after a 2 hours assay for Examples 11, 2, 8, 9, 10, 11, 12, 15, 16, 17, 18, and 20. As controls the comparative example 1 and 2 are shown. The cargos L-dopa, 5(6)-car boxyfluorescein, rhodamine b, quantum dots, superparamagnetic iron oxide nanoparticles (SPION), the peptide H-D-Ala-D-NMePhe-D-Nal(2)-D-Val-D-Leu-D-Lys-D-Lys-$NH_2$ (SEQ ID NO: 3) and antibody Avastin were not detected in the acceptor compartments after the 2 h assay.

| Reference compound | Compound | Papp (×10$^6$) cm/s | Transport (%) (2 h) |
|---|---|---|---|
| Comparative example 1 | H-L-Thr-L-His-L-Arg-L-Pro-L-Pro-L-Met-L-Trp-L-Ser-L-Pro-L-Val-L-Trp-L-Pro-$NH_2$ (SEQ ID NO: 5) | 12.5 ± 5.2 | 14.9 ± 2.5 |
| Comparative example 2 | H-D-Thr-D-His-D-Arg-D-Pro-D-Pro-D-Met-D-Trp-D-Ser-D-Pro-D-Val-D-Trp-D-Pro-$NH_2$ (SEQ ID NO: 6) | 9.9 ± 1.6 | 11.7 ± 6.4 |
| Cargo | L-Dopa | — | — |
| Cargo | 5(6)-carboxifluorescein | — | — |
| Cargo | Rhodamine b | — | — |
| Cargo | Quantum dot | — | — |
| Cargo | SPION | — | — |
| Cargo | H-D-Ala-D-NMePhe-D-Nal(2)-D-Val-D-Leu-D-Lys-D-Lys-$NH_2$ (SEQ ID NO: 3) | — | — |
| Cargo | Antibody Avastin partially reduced and trapped with Ellman's reagent | 0.054 ± 0.005 | 0.064 ± 0.006 |
| Example 1: | H-D-Pro-D-Trp-D-Val-D-Pro-D-Ser-D-Trp-D-Met-D-Pro-D-Pro-D-Arg-D-His-D-Thr-$NH_2$ (SEQ ID NO: 1) | 21.4 ± 2.1 | 25.1 ± 3 |
| Example 2: | H-Gly-D-Pro-D-Trp-D-Val-D-Pro-D-Ser-D-Trp-D-Met-D-Pro-D-Pro-D-Arg-D-His-D-Thr-$NH_2$ (SEQ ID NO: 2) | 19.4 ± 1.8 | 22.3 ± 2.6 |
| Example 8: | L-Dopa-D-Pro-D-Trp-D-Val-D-Pro-D-Ser-D-Trp-D-Met-D-Pro-D-Pro-D-Arg-D-His-D-Thr-$NH_2$ | 8.46 ± 2.1 | 10.1 ± 1.3 |
| Example 9: | 5(6)-carboxifluoresceina-D-Pro-D-Trp-D-Val-D-Pro-D-Ser-D-Trp-D-Met-D-Pro-D-Pro-D-Arg-D-His-D-Thr-$NH_2$ | 16.2 ± 1.3 | 17.1 ± 2.6 |
| Example 10: | Quantum dot-Gly-D-Pro-D-Trp-D-Val-D-Pro-D-Ser-D-Trp-D-Met-D-Pro-D-Pro-D-Arg-D-His-D-Thr-$NH_2$ | 0.27 ± 0.03 | 0.31 ± 0.02 |

TABLE 2-continued

Apparent permeability (Papp) and percentage of transport after a 2 hours assay for Examples 11, 2, 8, 9, 10, 11, 12, 15, 16, 17, 18, and 20. As controls the comparative example 1 and 2 are shown. The cargos L-dopa, 5(6)-car boxyfluorescein, rhodamine b, quantum dots, superparamagnetic iron oxide nanoparticles (SPION), the peptide H-D-Ala-D-NMePhe-D-NaI(2)-D-Val-D-Leu-D-Lys-D-Lys-NH$_2$ (SEQ ID NO: 3) and antibody Avastin were not detected in the acceptor compartments after the 2 h assay.

| Reference compound | Compound | Papp (×10$^6$) cm/s | Transport (%) (2 h) |
|---|---|---|---|
| Example 11: | SPION-Gly-D-Pro-D-Trp-D-Val-D-Pro-D-Ser-D-Trp-D-Met-D-Pro-D-Pro-D-Arg-D-His-D-Thr-NH$_2$ | 0.19 ± 0.07 | 0.22 ± 0.05 |
| Example 12: | H-D-Ala-D-NMePhe-D-NaI(2)-D-Val-D-Leu-D-Lys-D-Lys-D-Pro-D-Trp-D-Val-D-Pro-D-Ser-D-Trp-D-Met-D-Pro-D-Pro-D-Arg-D-His-D-Thr-NH$_2$ | 0.14 ± 0.01 | 0.2 ± 0.04 |
| Example 17: | Rhodamine b-L-Lys(Antibody)-D-Pro-D-Trp-D-Val-D-Pro-D-Ser-D-Trp-D-Met-D-Pro-D-Pro-D-Arg-D-His-D-Thr-NH$_2$ tech 3 (5 peptides/Ab). | 0.16 ± 0.10 | 0.13 ± 0.08 |
| Example 18: | Rhodamine b-L-Lys(Antibody)-D-Pro-D-Trp-D-Val-D-Pro-D-Ser-D-Trp-D-Met-D-Pro-D-Pro-D-Arg-D-His-D-Thr-NH$_2$ tech 4.1.A and 4.3 (2-3 peptides/Ab). | 0.18 ± 0.05 | 0.15 ± 0.04 |
| Example 20: | Rhodamine b-L-Lys(Antibody)-D-Pro-D-Trp-D-Val-D-Pro-D-Ser-D-Trp-D-Met-D-Pro-D-Pro-D-Arg-D-His-D-Thr-NH$_2$ tech 4.2 and 4.3 (8 peptides/Ab). | 0.36 ± 019 | 0.30 ± 0.16 |

The values of permeability equal to or higher than 1×10-6 cm/s are considered exceptionally good, and values equal to or higher than 0.1×10-6 cm/s are considered good. The permeability values depend highly on the cargo used. For a large cargo such as quantum dots or SPION values close to 0.1×10-6 cm/s and are considered to be very good.

Example 22

Stability of the Shuttle in Human Serum

One of the major advantage of the shuttles of this invention is that unlike the vast majority of peptides composed exclusively of L-amino acids (which are rapidly metabolized by a series of enzymes present in the serum of the blood, thus limiting their therapeutic effects), these are made with D-amino acids, thus are not recognized by the metabolic enzymes present in the serum, thereby increasing significantly their half-life in serum.

Regarding to the stability studies in human serum of the BBB-shuttles (examples 1 and 2) and the peptides presented in the comparative examples 1 and 2, these were incubated at a concentration of 150 μM in buffer HBSS at 37° C. in the presence of 90% human serum. At a range of times, 50 μL aliquots were collected to which methanol was added in order to precipitate the serum proteins. The samples were centrifuged, filtered and analysed by HPLC to determine the degree of degradation of the BBB-shuttle In Table 3, it can be observed how the shuttles with D-amino acids show a dramatic increase of its half-life time in human serum, while the version with L-amino acids (Comparative Example 1) is rapidly degraded.

In summary, the example 1 and 2 are about shuttle-stable proteases that have a surprisingly high transport through the blood-brain barrier.

TABLE 3 half-life time of the BBB-shuttle. Comparative Example 1 is shown as control.

| Reference compound | Compound | Half-life time in serum |
|---|---|---|
| Comparative example 1 | H-L-Thr-L-His-L-Arg-L-Pro-L-Pro-L-Met-L-Trp-L-Ser-L-Pro-L-Val-L-Trp-L-Pro-NH2 (SEQ ID NO: 5) | <1 h |
| Comparative example 2 | H-D-Thr-D-His-D-Arg-D-Pro-D-Pro-D-Met-D-Trp-D-Ser-D-Pro-D-Val-D-Trp-D-Pro-NH2 (SEQ ID NO: 6) | >24 h |
| Example 1 | H-D-Pro-D-Trp-D-Val-D-Pro-D-Ser-D-Trp-D-Met-D-Pro-D-Pro-D-Arg-D-His-D-Thr-NH2 (SEQ ID NO: 1) | >24 h |
| Example 2 | H-Gly-D-Pro-D-Trp-D-Val-D-Pro-D-Ser-D-Trp-D-Met-D-Pro-D-Pro-D-Arg-D-His-D-Thr-NH$_2$ (SEQ ID NO: 2) | >24 h |

The invention claimed is:

1. A compound of formula (I) or a pharmaceutically acceptable salt thereof, $$R_1-(X)_K-P-Y \qquad (I)$$

wherein:

$R_1$ is the group attached to the N-terminal of the first amino acid of the sequence P, optionally via the ligand X, and is selected from the group consisting of H, $CH_3C(=O)-$, and maleimide;

X is a biradical selected from the group consisting of $-NH-(CH_2)_r-C(=O)-$, $-C(=O)-(CH_2)_r-C(=O)-$, $-S(CH_2)_r-$, $-S-(CH_2)_r-C(=O)-$, $-O-(CH_2)_r-$, $-S-CH_2-CH(NH_2)-C(=O)-$, $-O-(CH_2)_r-C(=O)-$, $-(CH_2)_r-C(=O)-$, $-NH-O-CH_2-C(=O)-NH-(CH_2)_r-CH(NH_2)-C(=O)-$, $-(CH_2)_r-C(=O)-NH-(CH_2)_r-CH(NH_2)-C(=O)-$, and $-NH-(CH_2)_r-CH(NHC(=O)CH_2NH_2)-C(=O)-$; wherein the biradical X is attached to $R_1$ and to the N of the sequence P as follows: $R_1-NH-(CH_2)_r-C(=O)-N(H)_m-$, $R_1-C(=O)-(CH_2)_r-C(=O)-N(H)_m-$, $R_1-S-(CH_2)_r-N(H)_m-$, $R_1-S-(CH_2)_r-C(=O)-N(H)_m-$, $R_1-O-(CH_2)_r-N(H)_m-$, $R_1-S-CH_2-CH(NH_2)-C(=O)-N(H)_m-$, $R_1-O-(CH_2)_r-C(=O)-N(H)_m-$, $R_1-(CH_2)_r-C(=O)-N(H)_m-$, $R_1-NH-O-CH_2-C(=O)-NH-(CH_2)_r-CH(NH_2)-C(=O)-N(H)_m-$, $R_1-(CH_2)_r-C(=O)-NH-(CH_2)_r-CH(NH_2)-C(=O)-N(H)_m-$, and $R_1-NH-(CH_2)_r-CH(NHC(=O)CH_2NH_2)-C(=O)-N(H)_m-$;

r is an integer from 1 to 5;

P is a biradical of an amino acid sequence comprising the sequence D-Pro-D-Trp-D-Val-D-Pro-D-Ser-D-Trp-D-Met-D-Pro-D-Pro-D-Arg-D-His-D-Thr (SEQ ID NO: 1);

Y is the group attached to the C-terminal of the last amino acid of the sequence P, and is selected from the group consisting of $-NH_2$, $-OH$, $-OR_2$ and $-NHR_2$;

$R_2$ is a radical selected from the group consisting of $(C_1-C_6)$-alkyl and $(CH_2)_2-NH-C(=O)-CH_2-O-NH_2$;

k is an integer from 0 to 2;

m is an integer from 0 to 1;

with the proviso that when the biradical X is $-C(=O)(CH_2)_rC(=O)-$, then $R_1$ is H; with the proviso that when m is 1, then the nitrogen of the N-terminal amino acid of the sequence P, which is attached to the biradical X, is in the form of $-NH-$, and when m is 0, then the nitrogen of the N-terminal amino acid of the sequence P, which is attached to the biradical X, is in the form of "—N—"; and with the proviso that when $R_1$ is maleimide then the biradical X is $-C(=O)-(CH_2)_r-C(=O)-$, $-CH(NH_2)-C(=O)-$, $-(CH_2)_r-C(=O)-$, and $-(CH_2)_r-C(=O)-NH-(CH_2)_r-CH(NH_2)-C(=O)-$.

2. The peptide compound according to claim 1, wherein:

$R_1$ is the group attached to the N-terminal of the first amino acid of the sequence P, optionally via the ligand X, and is selected from the group consisting of H and $CH_3C(=O)-$;

X is a biradical selected from the group consisting of $-NH-(CH_2)_r-C(=O)-$, $-C(=O)-(CH_2)_r-C(=O)-$, $-S(CH_2)_r-$, $-S-(CH_2)_r-C(=O)-$, $-O-(CH_2)_r-$, $-S-CH_2-CH(NH_2)-C(=O)-$ and $-O-(CH_2)_r-C(=O)-$; wherein the biradical X is attached to $R_1$ and to the N of the sequence P as follows: $R_1-NH-(CH_2)_r-C(=O)-N(H)_m-$, $R_1-C(=O)-(CH_2)_r-C(=O)-N(H)_m-$, $R_1-S-(CH_2)_r-N(H)_m-$, $R_1-S-(CH_2)_r-C(=O)-N(H)_m-$, $R_1-O-(CH_2)_r-N(H)_m-$, $R_1-S-CH_2-CH(NH_2)-C(=O)-N(H)_m-$, and $R_1-O-(CH_2)_r-C(=O)-N(H)_m-$;

r is an integer from 1 to 3;

P is a biradical of an amino acid sequence comprising the sequence D-Pro-D-Trp-D-Val-D-Pro-D-Ser-D-Trp-D-Met-D-Pro-D-Pro-D-Arg-D-His-D-Thr (SEQ ID NO: 1);

Y is the group attached to the C-terminal of the last amino acid of the sequence P, and is selected from the group consisting of $-NH_2$, $-OH$, $-OR_2$, and $-NHR_2$;

$R_2$ is a radical $(C_1-C_6)$-alkyl;

k is an integer from 0 to 2;

m is an integer from 0 to 1;

with the proviso that when the biradical X is $-C(=O)(CH_2)_rC(=O)-$, then $R_1$ is H and with the proviso that when m is 1, then the nitrogen of the N-terminal amino acid of the sequence P, which is attached to the biradical X, is in the form of $-NH-$, and when m is 0, then the nitrogen of the N-terminal amino acid of the sequence P, which is attached to the biradical X, is in the form of "—N—".

3. The peptide compound according to claim 1, wherein P is a biradical consisting of SEQ ID NO: 1.

4. The peptide compound according to claim 1, where P is a biradical that is the sequence Gly-D-Pro-D-Trp-D-Val-D-Pro-D-Ser-D-Trp-D-Met-D-Pro-D-Pro-D-Arg-D-His-D-Thr- (SEQ ID NO: 2).

5. The peptide compound according to claim 1, wherein k is an integer from 0 to 1.

6. The peptide compound according to claim 1, wherein Y is selected from $-NH_2$, $-OH$ and $-NHR_2$.

7. The peptide compound according to claim 1, which is selected from the group consisting of:

H-D-Pro-D-Trp-D-Val-D-Pro-D-Ser-D-Trp-D-Met-D-Pro-D-Pro-D-Arg-D-His-D-Thr-$NH_2$ (Ia): and H-Gly-D-Pro-D-Trp-D-Val-D-Pro-D-Ser-D-Trp-D-Met-D-Pro-D-Pro-D-Arg-D-His-D-Thr-NH$_2$ (Ib).

8. A construct of formula (II) or a pharmaceutically acceptable salt thereof,

(II)

wherein:

X is a biradical selected from the group consisting of —NH—(CH$_2$)$_r$—C(=O)—, —C(=O)—(CH$_2$)$_r$—C(=O)—, —S(CH$_2$)$_r$—, —S—(CH$_2$)$_r$—C(=O)—, —O—(CH$_2$)$_r$—, —S—CH$_2$—CH(NH$_2$)—C(=O)—, —O—(CH$_2$)$_r$—C(=O)—, —(CH$_2$)$_r$—C(=O)—, —NH—O—CH$_2$—C(=O)—NH—(CH$_2$)$_r$—CH(NH$_2$)—C(=O)—, —(CH$_2$)$_r$—C(=O)—NH—(CH$_2$)$_r$—CH(NH$_2$)—C(=O), and —NH—(CH$_2$)$_r$—CH(NHC(=O)CH$_2$NH$_2$)—C(=O)—; wherein the biradical X is attached to R$_1$ and to the N of the sequence P as follows: R$_1$—NH—(CH$_2$)$_r$—C(=O)—NH$_m$—, R$_1$—C(=O)—(CH$_2$)$_r$—C(=O)—N(H)$_m$—, R$_1$—S—(CH$_2$)$_r$—N(H)$_m$—, R$_1$—S—(CH$_2$)$_r$—C(=O)—N(H)$_m$—, R$_1$—O—(CH$_2$)$_r$—N(H)$_m$—, R$_1$—S—CH$_2$—CH(NH$_2$)—C(=O)—N(H)$_m$—, R$_1$—O—(CH$_2$)$_r$—C(=O)—N(H)$_m$—, R$_1$—(CH$_2$)$_r$—C(=O)—N(H)$_m$—, R$_1$—NH—O—CH$_2$—C(=O)—NH—(CH$_2$)$_r$—CH(NH$_2$)—C(=O)—N(H)$_m$, R$_1$—(CH$_2$)$_r$—C(=O)—NH—(CH$_2$)$_r$—CH(NH$_2$)—C(=O)—N(H)$_m$, and R$_1$—NH—(CH$_2$)$_r$—CH(NHC(=O)CH$_2$NH$_2$)—C(=O)—N(H)$_m$;

r is an integer from 1 to 5;

P is a biradical of an amino acid sequence comprising the sequence D-Pro-D-Trp-D-Val-D-Pro-D-Ser-D-Trp-D-Met-S-Pro-D-Pro-D-Arg-D-His-D-Thr (SEQ ID NO: 1);

Y is the group attached to the C-terminal of the last amino acid of the sequence P, and is selected from the group consisting of —NH$_2$, —OH, —OR$_2$ and —NHR$_2$;

R$_2$ is a radical selected from the group consisting of (C$_1$-C$_6$)-alkyl and (CH$_2$)$_2$—NH—C(=O)—CH$_2$—O—NH$_2$;

k is an integer from 0 to 2;

q is an integer from 1 to 2, and

Z is a radical of a biologically active substance or a substance for use in a diagnostic method, said substance being substantially unable to cross the BBB by itself; wherein when q is 1, then Z is attached to the N-terminal of the first amino acid of the sequence P, either directly or via the ligand X, and when q is 2, then one Z is attached to the N-terminal of the first amino acid of the sequence P, either directly or via the ligand X, and the other Z is attached either to a nitrogen of the ligand X or to a nitrogen of the lateral chain of the first amino acid of the sequence P.

9. The construct of formula (II) according to claim 8, which has the formula (II')

(II')

wherein:

X, P, Y, k are as defined in claim 1, q is 1,

X is a biradical selected from the group consisting of —NH—(CH$_2$)$_r$—C(=O)—, —C(=O)—(CH$_2$)$_r$—C(=O)—, —S(CH$_2$)$_r$—, —S—(CH$_2$)$_r$—C(=O)—, —O—(CH$_2$)$_r$—, —S—CH$_2$—CH(NH$_2$)—C(=O)—, —O—(CH$_2$)$_r$—C(=O)—, —(CH$_2$)$_r$—C(=O)—, —NH—O—CH$_2$—C(=O)—NH—(CH$_2$)$_r$—CH(NH$_2$)—C(=O)—, —(CH$_2$)$_r$—C(=O)—NH—(CH$_2$)$_r$—CH(NH$_2$)—C(=O)—, and —NH—(CH$_2$)$_r$—CH(NHC(=O)CH$_2$NH$_2$)—C(=O)—; wherein the biradical X is attached to R$_1$ and to the N of the sequence P as follows: R$_1$—NH—(CH$_2$)$_r$—C(=O)—N(H)$_m$—, R$_1$—C(=O)—(CH$_2$)$_r$—C(=O)—N(H)$_m$—, R$_1$—S—(CH$_2$)$_r$—N(H)$_m$—, R$_1$—S—(CH$_2$)$_r$—C(=O)—N(H)$_m$—, R$_1$—O—(CH$_2$)$_r$—N(H)$_m$—, R$_1$—S—CH$_2$—CH(NH$_2$)—C(=O)—N(H)$_m$, R$_1$—O—(CH$_2$)$_r$—C(=O)—N(H)$_m$—, R$_1$—(CH$_2$)$_r$—C(=O)—N(H)$_m$, R$_1$—NH—O—CH$_2$—C(=O)—NH—(CH$_2$)$_r$—CH(NH$_2$)—C(=O)—N(H)$_m$, R$_1$—(CH$_2$)$_r$—C(=O)—NH—(CH$_2$)$_r$—CH(NH$_2$)—C(=O)—N(H)$_m$, and R$_1$—NH—(CH$_2$)$_r$—CH(NHC(=O)CH$_2$NH$_2$)—C(=O)—N(H)$_m$;

r is an integer from 1 to 5;

P is a biradical of an amino acid sequence comprising the sequence D-Pro-D-Trp-D-Val-D-Pro-D-Ser-D-Trp-D-Met-D-Pro-D-Pro-D-Arg-D-His-D-Thr (SEQ ID NO: 1);

Y is the group attached to the C-terminal of the last amino acid of the sequence P, and is selected from the group consisting of —NH$_2$, —OH, —OR$_2$ and —NHR$_2$;

R$_2$ is a radical selected from the group consisting of (C$_1$-C$_6$)-alkyl and (CH$_2$)$_2$—NH—CH$_2$—O—NH$_2$;

k is an integer from 0 to 2; and

Z is a radical of a biologically active substance or a substance for use in a diagnostic method, said substance being substantially unable to cross the BBB by itself.

10. The construct according to claim 8, wherein Z is a radical of an active pharmaceutical ingredient capable of forming an amide bond, an ester bond, a disulfide bond, a thioeter bond, an oxime bond, an amine bond, or an hydrazone bond with X, and is selected from the group consisting of antiretroviral agents, anticancer agents, antipsychotic agents, antineurodegenerative agents, replacement therapy agents, and antiepileptic agents.

11. The construct according to claim 10, wherein the pharmaceutical active agent is selected from the group consisting of an antibody, L-dopamine and H-D-Ala-D-NMePhe-D-Nal(2)-D-Val-D-Leu-D-Lys-D-Lys (SEQ ID NO: 3).

12. The construct according to claim 8, wherein Z is a radical of a compound selected from the group consisting of an antibody, 5(6)-carboxyfluorescein, Quantum dots, and Spion.

13. The construct according to claim 8, which is selected from the group consisting of:
L-Dopa-D-Pro-D-Trp-D-Val-D-Pro-D-Ser-D-Trp-D-Met-D-Pro-D-Pro-D-Arg-D-His-D-Thr-NH$_2$ (IIa);
H-D-Ala-D-NMePhe-D-Nal(2)-D-Val-D-Leu-D-Lys-D-Lys-D-Pro-D-Trp-D-Val-D-Pro-D-Ser-D-Trp-D-Met-D-Pro-D-Pro-D-Arg-D-His-D-Thr-NH$_2$ (IIb);
5(6)-carboxifluorescein-D-Pro-D-Trp-D-Val-D-Pro-D-Ser-D-Trp-D-Met-D-Pro-D-Pro-D-Arg-D-His-D-Thr-NH$_2$ (IIc);
Quantum dot-Gly-D-Pro-D-Trp-D-Val-D-Pro-D-Ser-D-Trp-D-Met-D-Pro-D-Pro-D-Arg-D-His-D-Thr-NH$_2$ (IId);
SPION-Gly-D-Pro-D-Trp-D-Val-D-Pro-D-S er-D-Trp-D-Met-D-Pro-D-Pro-D-Arg-D-His-D-Thr-NH$_2$ (IIe),
5(6)-Carboxifluorescein-L-Lys(Antibody)-D-Pro-D-Trp-D-Val-D-Pro-D-Ser-D-Trp-D-Met-D-Pro-D-Pro-D-Arg-D-His-D-Thr-NH$_2$ (IIf); and
Rhodamine b-L-Lys(Antibody)-D-Pro-D-Trp-D-Val-D-Pro-D-Ser-D-Trp-D-Met-D-Pro-D-Pro-D-Arg-D-His-D-Thr-NH$_2$ (IIg).

14. A pharmaceutical composition or a composition for diagnostic purposes comprising a therapeutically effective amount of the construct as defined in claim 8, together with appropriate amounts of pharmaceutically acceptable carriers or excipients and/or acceptable carriers or excipients for diagnosis.

15. A method for the treatment of Parkinson's disease, comprising administering to a mammal in need thereof a therapeutically effective amount of a construct of formula (II) as defined in claim 8, where Z is a radical of dopamine, together with pharmaceutically excipients or carriers.

16. A method for the treatment of Alzheimer's disease, comprising administering to a mammal in need thereof a therapeutically effective amount of a construct of formula (II) as defined in claim 8, wherein Z is a peptidic radical of the peptide H-D-Ala-D-NMePhe-D-Nal(2)-D-Val-D-Leu-D-Lys-D-Lys-NH$_2$ (SEQ ID NO: 3) together with pharmaceutically excipients or carriers.

17. A method for the diagnosis of a disease comprising
  administering to a mammal in need of such diagnostic, a
    therapeutically effective amount of the construct of formula (II) as defined in claim 8 wherein Z is a superparamagentic iron oxide nanoparticle, a gadolinium complex, or a manganese complex, together with one or more pharmaceutically acceptable excipients or carriers and/or acceptable carriers or excipients for diagnosis,
generating an image by magnetic resonance imaging, and making a diagnosis using this image.

18. A method for the diagnosis of a disease comprising
  administering to a mammal in need of such diagnostic, a
    therapeutically effective amount of the construct of formula (II) as defined in claim 8 wherein Z is selected from a group consisting of 5(6)-carboxyfluorescein, Texas red, and rhodamine and quantum dots, together with one or more pharmaceutically acceptable excipients or carriers and/or acceptable carriers or excipients for diagnosis,
generating an image using dual photon microscopy, and making a diagnosis using this image.

* * * * *